US011549135B2

(12) United States Patent
Engreitz

(10) Patent No.: US 11,549,135 B2
(45) Date of Patent: Jan. 10, 2023

(54) OLIGONUCLEOTIDE-COUPLED ANTIBODIES FOR SINGLE CELL OR SINGLE COMPLEX PROTEIN MEASUREMENTS

(71) Applicants: THE BROAD INSTITUTE, INC., Cambridge, MA (US); PRESIDENT AND FELLOWS OF HARVARD COLLEGE, Cambridge, MA (US)

(72) Inventor: Jesse Engreitz, Cambridge, MA (US)

(73) Assignees: THE BROAD INSTITUTE, INC., Cambridge, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 272 days.

(21) Appl. No.: 16/570,621

(22) Filed: Sep. 13, 2019

(65) Prior Publication Data
US 2020/0087707 A1 Mar. 19, 2020

Related U.S. Application Data

(60) Provisional application No. 62/731,721, filed on Sep. 14, 2018.

(51) Int. Cl.
| | | |
|---|---|---|
| *C12Q 1/6806* | (2018.01) | |
| *C12Q 1/6869* | (2018.01) | |
| *C12Q 1/6855* | (2018.01) | |
| *C40B 70/00* | (2006.01) | |

(52) U.S. Cl.
CPC ........ *C12Q 1/6806* (2013.01); *C12Q 1/6855* (2013.01); *C12Q 1/6869* (2013.01); *C12Q 2563/107* (2013.01); *C12Q 2565/1015* (2013.01); *C40B 70/00* (2013.01)

(58) Field of Classification Search
CPC .. C12Q 1/6806; C12Q 1/6855; C12Q 1/6869; C12Q 1/6804; C12Q 2563/179; C12Q 2531/113; C12Q 2563/159; C12Q 2563/107; C12Q 2565/514; C12Q 2521/501; C12Q 2525/161; C40B 70/00
See application file for complete search history.

(56) References Cited

U.S. PATENT DOCUMENTS

| | | |
|---|---|---|
| 2006/0078888 A1 | 4/2006 | Griffiths et al. |
| 2016/0305856 A1 | 10/2016 | Boyden et al. |
| 2017/0067096 A1 | 3/2017 | Wassie et al. |
| 2018/0024139 A1 * | 1/2018 | Peikon ............. C12Q 1/6804 506/4 |

FOREIGN PATENT DOCUMENTS

| | | |
|---|---|---|
| WO | 2014047556 A1 | 3/2014 |
| WO | 2014047561 A1 | 3/2014 |
| WO | 2014143158 A1 | 9/2014 |
| WO | 2015127183 A1 | 8/2015 |
| WO | WO-2016145409 A1 * | 9/2016 ......... G01N 33/6845 |

OTHER PUBLICATIONS

Islam, Saiful et al., "Quantitative single-cell rna-seq with unique molecular identifiers," Nature Methods, vol. 11, No. 2, pp. 163-166, Feb. 2014.
Hendel, Ayal et al., "Chemically modified guide RNAs enhance CRISPR-Cas genome editing in human primary cells," Nat Biotechnol., vol. 33, No. 9, pp. 985-989, Sep. 2015.
Rahdara, Meghdad et al., "Synthetic CRISPR RNA-Cas9-guided genome editing in human cells," PNAS, pp. E7110-E7117, Published online Nov. 16, 2015.
Allerson, Charles et al., "Fully 2'-Modified Oligonucleotide Duplexes with Improved in Vitro Potency and Stability Compared to Unmodified Small Interfering RNA," J. Med. Chem., vol. 48, pp. 901-904, 2005.
Bramsen, Jesper B. et al., "Development of therapeutic-grade small interfering RNAs by chemical engineering," Front. Genet., vol. 3, Article 154, pp. 1-22, Aug. 20, 2012.
Deng, Wulan et al., "CASFISH: CRISPR/Cas9-mediated in situ labeling of genomic loci in fixed cells," PNAS, vol. 112, No. 38, pp. 11870-11875, Sep. 22, 2015.
Sharma, Vivek K. et al., "Antisense oligonucleotides: modifications and clinical trials," MedChemComm., vol. 5, pp. 1454-1471, 2014.
Li, Bin et al., "Engineering CRISPR-Cpf1 crRNAs and mRNAs to maximize genome editing efficiency," Nature Biomedical Engineering, vol. 1, No. 5, pp. 1-21, May 2017.
Ryan, Daniel E. et al., "Improving CRISPR-Cas specificity with chemical modifications in single-guide RNAs," Nucleic Acids Res., vol. 46, No. 2, pp. 792-803, Published online Dec. 4, 2017.

(Continued)

*Primary Examiner* — Narayan K Bhat
(74) *Attorney, Agent, or Firm* — F. Brent Nix, Esq.; Johnson, Marcou, Isaacs & Nix, LLC

(57) ABSTRACT

Provided herein are compositions and methods for simultaneously measuring target oligonucleotides and protein in single cells. Compositions comprise an antibody-tagged oligonucleotide, including an origin specific barcode handle sequence, a first primer handle sequence, a second primer handle sequence, and a target binding region. The composition may also include an adapter sequence, a unique molecular identifier (UMI), and a poly-A sequence. Methods for simultaneously measuring target oligonucleotides and protein in single cells generally involve delivering a mixture of the composition to a population of cells and encapsulating individual cells in an individual discrete volume comprising PCR primers on a bead. The individual discrete volume may be suspended in a reverse transcription mixture and the nucleotide sequence of the origin specific barcode handle sequence may be detected, thereby assigning the target oligonucleotide and protein of interest to a specific individual discrete volume, while maintaining information about sample origin of the target oligonucleotide.

103 Claims, 1 Drawing Sheet
Specification includes a Sequence Listing.

(56) References Cited

OTHER PUBLICATIONS

Kress, W. John et al., "Use of DNA barcodes to identify flowering plants," PNAS., vol. 102, No. 23, pp. 8369-8374, Jun. 7, 2005.
Koch, H., "Combining morphology and DNA barcoding resolves the taxonomy of Western Malagasy Liotrigona Moure," African Invertebrates, vol. 51 (2), pp. 413-421, Dec. 2010.
Seberg, Ole et al., "How many loci does it take to DNA barcode a crocus?," PLoS One | vol. 4 | Issue 2 | e4598 pp. 1-6 | Feb. 2009.
Soininen, Eeva et al., "Analysing diet of small herbivores: the efficiency of DNA barcoding coupled with high-throughput pyrosequencing for deciphering the composition of complex plant mixtures," Frontiers in Zoology, vol. 6, No. 16, pp. 1-9, Accepted: Aug. 20, 2009.
CBOL Plant Working Groupl et al., "A DNA barcode for land plants," PNAS, vol. 106, No. 31, pp. 12794-12797, Aug. 4, 2009.
Kress, W. John et al., "DNA barcodes: Genes, genomics, and bioinformatics" PNAS, vol. 105, No. 8, pp. 2761-2762, Feb. 26, 2008.
Lahaye, Renaud et al., "DNA barcoding the floras of biodiversity hotspots," PNAS, vol. 105, No. 8, pp. 2923-2928, Feb. 26, 2008.
Ausubel, J.H, "A botanical macroscope," PNAS, vol. 106, No. 31, pp. 12569-12570, Aug. 4, 2009.
Birrell, Geoff W., et al., "A genome-wide screen in Saccharomyces cerevisiae for genes affecting UV radiation sensitivity," PNAS, vol. 98, No. 22, pp. 12608-12613, Oct. 23, 2001.
Giaever, et al., "Functional profiling of the *Saccharomyces cerevisiae* genome," Nature, vol. 418, pp. 387-391, Jul. 25, 2002.
Winzeler, Elizabeth A. et al., "Functional Characterization of the *S. cerevisiae* Genome by Gene Deletion and Parallel Analysis," Science, vol. 285, 901-906, Aug. 6, 1999.
Xu, Qikai et al., "Design of 240,000 orthogonal 25mer DNA barcode probes," PNAS, vol. 106, No. 7, pp. 2289-2294, Feb. 17, 2009.
Chung, Kwanghun et al., "Structural and molecular interrogation of intact biological systems," Nature, vol. 497, No. 7449, pp. 322-337, May 16, 2013.
Mocanu, Maria-Magdalena et al., "Comparative analysis of fluorescence resonance energy transfer (FRET) and proximity ligation assay (PLA)," Proteomics, vol. 11, No. 10, pp. 2063-2070, Accepted: Feb. 11, 2011.
Soderberg, Ola et al., "Direct observation of individual endogenous protein complexes in situ by proximity ligation," Nature Methods, vol. 3, No. 12, pp. 995-1000, Dec. 2006.
Stoeckius, Marion et al., "Large-scale simultaneous measurement of epitopes and transcriptomes in single cells," Nature Methods, vol. 14, No. 9, pp. 865-868, Sep. 2017.
Quinodoz, Sofia A. et al., "Higher-order inter-chromosomal hubs shape 3-dimensional genome organization in the nucleus," BioRxiv, pp. 1-69, Nov. 18, 2017.
Moon, T. K., "Error Correction Coding: Mathematical Methods and Algorithms," Wiley, New York, ed. 1, 2005.

* cited by examiner

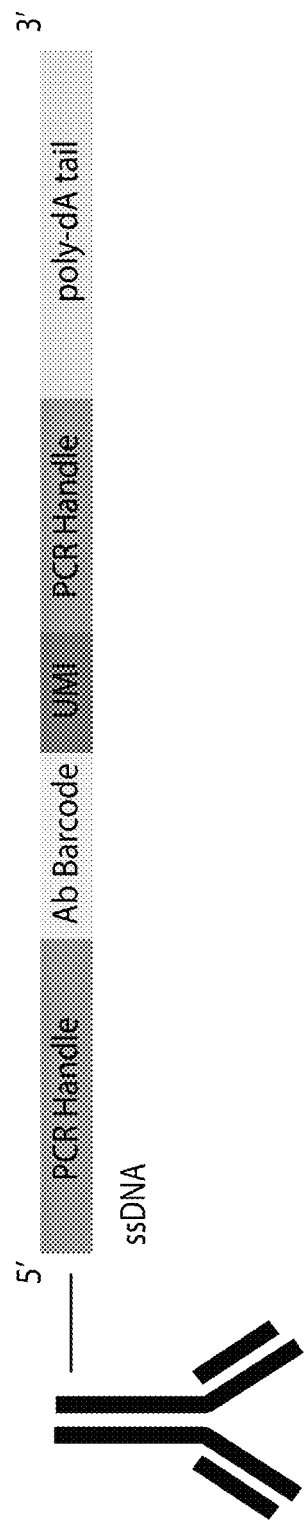
Example Oligo Sequence:
CACCCGAGAATTCCA CCTGGTAG NNNNNN CTCGATAGCC AAAAAAAAAAAAAAAAAAAAAAAAAAAA

OLIGONUCLEOTIDE-COUPLED ANTIBODIES FOR SINGLE CELL OR SINGLE COMPLEX PROTEIN MEASUREMENTS

CROSS-REFERENCE TO RELATED APPLICATIONS

This application claims the benefit of U.S. Provisional Application No. 62/731,721, filed Sep. 14, 2018. The entire contents of the above-identified applications are hereby fully incorporated herein by reference.

TECHNICAL FIELD

The subject matter disclosed herein is generally directed to compositions and methods for detection of target nucleic acids and proteins in single cells.

REFERENCE TO AN ELECTRONIC SEQUENCE LISTING

The contents of the electronic sequence listing (BROD_2540_ST25.txt"; Size is 1,393 bytes and it was created on Sep. 9, 2019) is herein incorporated by reference in its entirety.

BACKGROUND

Currently available targeted methods for simultaneously measuring transcripts and proteins in single cells are limited in scale and/or can only profile a few genes and proteins in parallel. Recent high-throughput single-cell sequencing approaches have been transformative for understanding complex cell populations and for studying the RNA expression patterns of individual cells in a heterogeneous population. However, simultaneous measurement of multiple types of macromolecules (such as that of RNA expression, DNA sequence, and protein abundance) in the same cell remains challenging. Similarly, such methods are unable to provide additional phenotypic information, such as protein levels of cell-surface markers.

Thus, there is a need for multipurpose compositions and methods that allow for simultaneous measurements of protein and nucleic acid abundance either in single cells or in individual molecule complexes.

SUMMARY

In one aspect, the invention provides a composition comprising a protein binding molecule bound to an oligonucleotide. The oligonucleotide comprises an origin specific barcode sequence, a first primer handle sequence, a second primer handle sequence, and a target binding region. In some embodiments, the composition may further comprise an adapter sequence. In some embodiments, the oligonucleotide may further comprise a unique molecular identifier (UMI). The protein binding molecule may be an antibody, aptamer, peptide, avimer, small molecule, recombinant protein, protein-binding derivative, or nucleic acid molecule. In specific embodiments, the protein binding molecule is an antibody. The oligonucleotide may comprise single stranded RNA, single-stranded or double-stranded DNA or may be a synthetic oligonucleotide. The oligonucleotide may further comprise a poly-A sequence. In some embodiments, the first primer handle sequence comprises SEQ ID NO:1 and the second primer handle sequence comprises SEQ ID NO:2.

In another aspect, the invention provides a method for simultaneously measuring target oligonucleotides and protein in single cells. Such a method may comprise delivering a mixture of any of the compositions described herein to a population of cells. The method may further comprise encapsulating individual cells in an individual discrete volume. The individual discrete volume may comprise PCR primers on a bead. The individual discrete volume may be suspended in a reverse transcription mixture and the nucleotide sequence of the origin specific barcode sequence may be detected, thereby assigning the target oligonucleotide and protein of interest to a specific individual discrete volume, while maintaining information about sample origin of the target oligonucleotide.

In some embodiments, the protein binding molecule is an antibody. In some embodiments, detecting the nucleotide sequence of the origin specific barcode sequence comprises nucleic acid sequencing, amplification, hybridization, or any combination thereof. In some embodiments, the individual discrete volume is a hydrogel droplet.

In some embodiments, the method further comprises methods for visualizing nucleic acids. In some embodiments, the methods for visualizing nucleic acids comprise direct fluorescence hybridization.

In some embodiments, the oligonucleotide is single-stranded or double-stranded DNA, RNA, or a synthetic oligonucleotide. In some embodiments, the synthetic oligonucleotide is a peptide nucleic acid. In some embodiments, the oligonucleotide comprises single-stranded RNA.

In some embodiments, the method comprises quantifying expression of single-stranded RNA, mRNA and genomic RNA simultaneously. In some embodiments, the target binding region is sequence specific. In some embodiments, the target oligonucleotide comprises DNA, RNA, lincRNA, mRNA, viral RNAs, or a combination thereof.

In some embodiments, each protein binding molecule bound to an oligonucleotide is an oligonucleotide-tagged protein binding molecule that further comprises a poly-A sequence.

In other embodiments, the method may further comprise admixing the population of cells with monomers of a polymerizable hydrogel and polymerizing the gel in an oil emulsion under conditions that allow covalent anchoring of nucleic acids and/or proteins to the hydrogel, wherein individual cells are encapsulated in the individual discrete volume. The emulsions may then be broken to release the individual discrete volume. The oligonucleotide-tagged protein binding molecules may then be added, either before or after hydrogel polymerization, PCR may be performed in the individual discrete volumes, wherein cell-barcoded amplicons are generated, and the resulting amplicons may be sequenced.

In some embodiments, the cells are fixed before preparing the hydrogel droplets. In some embodiments, the method allows for measuring of both intracellular and extracellular proteins.

In yet another aspect, the invention provides a method for measuring proteins in single cells comprising delivering a mixture of any of the compositions described herein to a population of cells, encapsulating individual cells in an individual discrete volume, wherein the individual discrete volume comprises PCR primers on a bead, amplifying the oligonucleotide of the composition using PCR, and quantifying target protein abundance and/or determining target protein localization based at least in part on sequencing of amplicons.

In some embodiments, the protein binding molecule is an antibody. In some embodiments, detecting the nucleotide sequence of the origin specific barcode sequence comprises nucleic acid sequencing, amplification, hybridization, or any combination thereof. In some embodiments, the individual discrete volume is a hydrogel droplet.

Some embodiments further comprise methods for visualizing nucleic acids. In some embodiments, methods for visualizing nucleic acids comprise direct fluorescence hybridization. In some embodiments, the oligonucleotide is single-stranded or double-stranded DNA, RNA, or a synthetic oligonucleotide. In some embodiments, the synthetic oligonucleotide is a peptide nucleic acid. In some embodiments, the target binding region is sequence specific.

Some embodiments further comprise measurement of target oligonucleotides in addition to protein, wherein the target oligonucleotides comprise DNA, RNA, lincRNA, mRNA, viral RNAs, or a combination thereof. In some embodiments, each protein binding molecule bound to an oligonucleotide is an oligonucleotide-tagged protein binding molecule that further comprises a poly-A sequence.

Some embodiments further comprise delivering one or more ligation dependent probes to the cells, wherein the one or more ligation dependent probe comprise i) sequences that bind in proximate locations on a target RNA, and ii) the first primer handle sequence, the second primer handle sequence, or both; linking the bound proximity probes; amplifying the oligonucleotide of the composition and the linked ligation dependent probes using barcoded PCR primers, wherein the barcode is incorporated into each resulting amplicon, and quantifying target protein abundance and/or determining target protein localization based at least in part on sequencing of amplicons.

In some embodiments, the one or more ligation dependent probes are linked by ligation, splinted ligation, hybridization, or proximity extension. In some embodiments, the one or more ligation dependent probes are molecular inversion probes (MIPs), padlock probes, or split-ligation probes, each probe further comprising a unique molecular identifier (UMI).

Some embodiments further comprise admixing the population of cells with monomers of a polymerizable hydrogel and polymerizing the gel in an oil emulsion under conditions that allow covalent anchoring of nucleic acids and/or proteins to the hydrogel, wherein individual cells are encapsulated in the individual discrete volume. The emulsions may then be broken to release the individual discrete volume, oligonucleotide-tagged protein binding molecules may then be added, either before or after hydrogel polymerization, PCR may be performed in the individual discrete volumes, wherein cell-barcoded amplicons are generated. The resulting amplicons may then be sequenced.

In some embodiments, the cells are fixed before preparing the hydrogel droplets. In some embodiments, the method allows for measuring of both intracellular and extracellular proteins.

In yet another aspect, the invention provides a method for determining the quantity and location of proteins within single cells comprising encapsulating cells or tissue in a hydrogel, treating the cells or tissue with any of the compositions described herein, delivering one or more ligation dependent probes to the cells, wherein the ligation dependent probe comprises a sequence that is complementary to the first primer handle sequence and a sequence that is complementary to the second primer handle sequence, amplifying the oligonucleotide of the composition using the ligation dependent probes, wherein the amplified oligonucleotide is incorporated into each resulting amplicon; and quantifying target protein abundance and/or determining target protein localization based at least in part on sequencing of amplicons.

In some embodiments, the protein binding molecule is an antibody. In some embodiments, the cells are fixed before delivering the ligation dependent probes. In some embodiments, the amplification reagents are rolling circle amplification reagents. In some embodiments, the ligation dependent probes are molecular inversion probes (MIPs), padlock probes, or split-ligation probes.

Some embodiments further comprise delivering one or more additional ligation dependent probes to the cells for measuring target mRNA. In some embodiments, the individual discrete volumes are hydrogel droplets.

Some embodiments further comprise methods for visualizing proteins. Such methods may comprise in situ imaging. Some embodiments further comprise a reporter sequence that enables cellular recording. In some embodiments, amplicons are sequenced using a fluorescence in situ sequencing method.

In yet another aspect, the invention provides a method for quantifying protein in individual molecule complexes comprising fixing a population of cells such that oligonucleotide-protein complexes are formed, delivering a mixture of any of the compositions described herein to the oligonucleotide-protein complexes, encapsulating complexes in an individual discrete volume, wherein the individual discrete volume comprises PCR primers on a bead, suspending the individual discrete volume in a reverse transcription mixture, and detecting the nucleotide sequence of the origin specific barcode sequence, thereby assigning the target oligonucleotide and protein of interest to a specific individual discrete volume, while maintaining information about sample origin of the target oligonucleotide.

In some embodiments, the protein binding molecule is an antibody. In some embodiments, detecting the nucleotide sequence of the origin specific barcode sequence comprises nucleic acid sequencing, amplification, hybridization, or any combination thereof. In some embodiments, the individual discrete volume is a hydrogel droplet. Some embodiments, further comprise methods for visualizing nucleic acids. Such methods may include direct fluorescence hybridization.

In some embodiments, the oligonucleotide is single-stranded or double-stranded DNA, RNA, or a synthetic oligonucleotide. The oligonucleotide may comprise single-stranded RNA. In some embodiments, the method comprises quantifying expression of single-stranded RNA, mRNA and genomic RNA simultaneously. In some embodiments, the synthetic oligonucleotide is a peptide nucleic acid.

In some embodiments, the target binding region is sequence specific. In some embodiments, the target oligonucleotide comprises DNA, RNA, lincRNA, mRNA, viral RNAs, or a combination thereof.

In some embodiments, each protein binding molecule bound to an oligonucleotide is an oligonucleotide-tagged protein binding molecule that further comprises a poly-A sequence.

Some embodiments further comprise admixing the oligonucleotide-protein complexes with monomers of a polymerizable hydrogel and polymerizing the gel in an oil emulsion under conditions that allow covalent anchoring of nucleic acids and/or proteins to the hydrogel, wherein individual complexes are encapsulated in the individual discrete volume, breaking the emulsions to release the individual discrete volume, adding oligonucleotide-tagged protein binding molecules, either before or after hydrogel polymerization, performing PCR in the individual discrete volumes, wherein cell-barcoded amplicons are generated, and sequencing the resulting amplicons.

In some embodiments, the complexes are fixed before preparing the hydrogel droplets. In some embodiments, the method allows for measuring of both intracellular and extracellular proteins.

In yet another aspect, the invention provides a method for quantifying protein in individual molecule complexes comprising fixing a population of cells, lysing the cells, and encapsulating the resulting individual molecule complexes with any of the compositions described herein in an individual discrete volume. The individual discrete volume may comprise PCR primers on a bead, the oligonucleotide of the composition may be amplified using PCR, and target protein abundance may be quantified and/or target protein localization may be determined based at least in part on sequencing of amplicons.

In some embodiments, the protein binding molecule is an antibody. In some embodiments, detecting the nucleotide sequence of the origin specific barcode sequence comprises nucleic acid sequencing, amplification, hybridization, or any combination thereof.

In some embodiments, the individual discrete volume is a hydrogel droplet. Some embodiments further comprise methods for visualizing nucleic acids. In some embodiments, the methods for visualizing nucleic acids comprise direct fluorescence hybridization.

In some embodiments, the oligonucleotide is single-stranded or double-stranded DNA, RNA, or a synthetic oligonucleotide. In some embodiments, the synthetic oligonucleotide is a peptide nucleic acid. In some embodiments, the target binding region is sequence specific.

Some embodiments further comprise measurement of target oligonucleotides in addition to protein, and wherein the target oligonucleotides comprise DNA, RNA, lincRNA, mRNA, viral RNAs, or a combination thereof.

In some embodiments, each protein binding molecule bound to an oligonucleotide is an oligonucleotide-tagged protein binding molecule that further comprises a poly-A sequence.

Some embodiments of this method further comprise delivering one or more ligation dependent probes to the oligonucleotide-protein complexes, wherein the one or more ligation dependent probe comprises i) sequences that bind in proximate locations on a target RNA, and ii) the first primer handle sequence, the second primer handle sequence, or both, linking the bound proximity probes; amplifying the oligonucleotide of the composition and the linked ligation dependent probes using barcoded PCR primers, wherein the barcode is incorporated into each resulting amplicon, and quantifying target protein abundance and/or determining target protein localization based at least in part on sequencing of amplicons.

Some embodiments further comprise admixing the oligonucleotide-protein complexes with monomers of a polymerizable hydrogel and polymerizing the gel in an oil emulsion under conditions that allow covalent anchoring of nucleic acids and/or proteins to the hydrogel, wherein individual complexes are encapsulated in the individual discrete volume, breaking the emulsions to release the individual discrete volume, adding oligonucleotide-tagged protein binding molecules, either before or after hydrogel polymerization, performing PCR in the individual discrete volumes, wherein cell-barcoded amplicons are generated, and sequencing the resulting amplicons.

In some embodiments, the cells are fixed before preparing the hydrogel droplets. In some embodiments, the method allows for measuring of both intracellular and extracellular proteins.

In yet another aspect, the invention provides a molecular assay system comprising a) a set of oligonucleotide-tagged protein binding molecules; b) amplification reagents; and c) droplet forming reagents for formation of hydrogel-based droplets. In some embodiments, the oligonucleotide-tagged protein binding molecules comprise an origin specific barcode sequence, a first primer handle sequence, a second primer handle sequence, and a target binding region.

In some embodiments, the oligonucleotide-tagged protein binding molecules further comprise an adapter sequence. In some embodiments, the oligonucleotide-tagged protein binding molecules further comprise a UMI.

In some embodiments, the protein binding molecules are antibodies, aptamers, peptides, avimers, small molecules, recombinant proteins, protein-binding derivatives, or nucleic acid molecules. In specific embodiments, the protein binding molecules are antibodies.

In some embodiments, the oligonucleotides comprise single-stranded RNA. In some embodiments, the oligonucleotides comprise single-stranded or double-stranded DNA or synthetic oligonucleotides. In some embodiments, the oligonucleotides further comprise a poly-A sequence.

In some embodiments, the first primer handle sequence comprises SEQ ID NO:1 and the second primer handle sequence comprises SEQ ID NO:2. Some embodiments further comprise a set of ligation dependent probes.

In some embodiments, the amplification reagents are whole genome amplification regents, PCR amplification reagent, reverse transcription reagents, rolling circle amplification reagents, or a combination thereof.

In some embodiments, the ligation dependent probes are molecular inversion probes (MIPs), padlock probes, or split-ligation probes.

In yet another aspect, the invention provides a kit comprising a) a panel of oligonucleotides, each oligonucleotide comprising an origin specific barcode sequence, a first primer handle sequence, a second primer handle sequence, and a target binding region; b) a panel of protein binding molecules; and c) optionally, reagents for coupling the protein binding molecules to the oligonucleotides.

In some embodiments, the oligonucleotides and the protein binding molecules are coupled together. In some embodiments, the protein binding molecules are antibodies, aptamers, peptides, avimers, small molecules, recombinant proteins, protein-binding derivatives, or nucleic acid molecules. In specific embodiments, the protein binding molecules are antibodies.

In some embodiments, the antibodies target receptors on immune cells. In other embodiments, the antibodies target specific markers in intracellular signaling pathways. In yet other embodiments, the antibodies target transcription factors.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 1—illustrates an exemplary composition and sequence thereof as described herein. Also shown is an exemplary oligonucleotide sequence (SEQ ID NO:3).

The FIGURES herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, the term "amplification" generally refers to increasing the number of copies of a nucleic acid molecule, such as a nucleic acid molecule that includes an indexable nucleic acid identifier, such as an origin-specific barcode as described herein. The resulting amplification products are typically called "amplicons." Amplification of a nucleic acid molecule (such as a DNA or RNA molecule) refers to use of a technique that increases the number of copies of a nucleic acid molecule (including fragments). In some examples, an amplicon is a nucleic acid from a cell, or a cellular system, such as mRNA or DNA that has been amplified.

The term "barcode" or "barcode sequence" as used herein, refers to any unique, non-naturally occurring, nucleic acid sequence that may be used to identify the originating source of a nucleic acid fragment. Such barcodes may be sequences including but not limited to, TTGAGCCT, AGTTGCTT, CCAGTTAG, ACCAACTG, GTATAACA or CAGGAGCC. Although it is not necessary to understand the mechanism of an invention, it is believed that the barcode sequence provides a high-quality individual read of a barcode associated with a viral vector, labeling ligand, shRNA, sgRNA or cDNA such that multiple species can be sequenced together.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogsteen binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention.

Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide compositions and methods for simultaneously measuring target oligonucleotides and protein in single cells or for quantifying protein in individual molecule complexes. Such compositions may comprise a protein binding molecule and an oligonucleotide tag. The protein binding molecule allows for binding to one or more target proteins. The oligonucleotide tag may be used to encode identifying information about the binding specificity of a protein binding molecule and/or enable amplification and detection of said target proteins. The compositions disclosed herein may be used in methods to perform simultaneous RNA and protein measurements, conduct single cell protein measurements, determine in situ measurements of protein abundance and localization, conduct single-complex protein measurements and identification, and other similar methods wherein detection of proteins by sequencing and/or hybridization is desired and/or where simultaneous detection of proteins and oligonucleotides, such as RNA, is needed.

Methods for simultaneously measuring target oligonucleotides and protein in single cells generally involve delivering a mixture of any of the compositions described herein to a population of cells and encapsulating individual cells in an individual discrete volume. The individual discrete volume may comprise PCR primers on a bead. The individual discrete volume may be suspended in a reverse transcription mixture and the nucleotide sequence of the origin specific barcode sequence may be detected, thereby assigning the target oligonucleotide and protein of interest to a specific individual discrete volume, while maintaining information about sample origin of the target oligonucleotide.

Methods for quantifying protein in individual molecule complexes generally involve fixing a population of cells, lysing the cells, and encapsulating the resulting individual molecule complexes with any of the compositions described herein in an individual discrete volume. The individual discrete volume may comprise PCR primers on a bead. The oligonucleotide of the composition may be amplified using PCR, and target protein abundance may be quantified and/or target protein localization may be determined based at least in part on sequencing of amplicons.

One advantage of the systems and methods described herein is that construct as described herein can be used for many different applications.

Constructs

Disclosed herein are constructs comprising a protein binding molecule and an oligonucleotide tag. The protein binding molecule may be any molecule that specifically binds to a polypeptide. Examples of specific polypeptide binding interactions include receptor:ligand, enzyme:substrate, antibody:antigen. The oligonucleotide tag may comprise an origin specific barcode handle sequence, a first primer handle sequence, a second primer handle sequence, and a target binding region. Among other features, the composition may further comprise an adapter sequence, a unique molecular identifier (UMI), and a poly-A sequence. In some embodiments, the poly-A sequence may be target specific.

Protein Binding Molecule

In certain example embodiments a protein binding molecule may be an oligonucleotide, a polypeptide, a lipid, a glycolipid, a polysaccharide, or chemical compound that binds to another polypeptide. Example protein binding molecules include, but are not limited to, antibody, aptamer, peptide, avimer, small molecule, recombinant protein, protein-binding derivative, or nucleic acid molecule.

In certain example embodiments, the protein binding molecule is an oligonucleotide-based protein binding molecule. The oligonucleotide-based protein binding molecule may comprise RNA, DNA, RNA/DNA hybrids, synthetic oligonucleotides or combinations thereof. Synthetic oligonucleotides include chemically synthesized deoxyribonucleotide or ribonucleotide polymers including without limitation, cDNA, mRNA, genomic DNA, and synthetic DNA or RNA or hybrids thereof. The nucleic acid can be double-stranded (ds) or single-stranded (ss). Where single-stranded, the nucleic acid can be the sense strand or the antisense strand. Nucleic acids can include natural nucleotides (such as A, T/U, C, and G), and can also include analogs of natural nucleotides, such as labeled nucleotides. Some examples of nucleic acids include the probes disclosed herein.

The major building blocks for polymeric nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major building blocks for polymeric nucleotides of RNA are adenosine 5'-triphosphate (ATP or A), guanosine 5'-triphosphate (GTP or G), cytidine 5'-triphosphate (CTP or C) and uridine 5'-triphosphate (UTP or U).

In some examples, nucleotides include those nucleotides containing modified bases, modified sugar moieties, and modified phosphate backbones, for example as described in U.S. Pat. No. 5,866,336 to Nazarenko et al. Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N~6-isopentenyladenine, 1-methylguanine, 1-methylinosine, 2,2-dimethylguanine, 2-methyladenine, 2-methylguanine, 3-methylcytosine, 5-methyl cytosine, N6-adenine, 7-methylguanine, 5-methylaminomethyluracil, methoxyaminomethyl-2-thiouracil, beta-D-mannosylqueuosine, 5'-methoxycarboxymethyluracil, 5-methoxyuracil, 2-methylthio-N6-isopentenyladenine, uracil-5-oxyacetic acid, pseudouracil, queuosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil, 2,6-diaminopurine and biotinylated analogs, amongst others. Examples of modified sugar moieties which may be used to modify nucleotides at any position on its structure include, but are not limited to arabinose, 2-fluoroarabinose, xylose, and hexose, or a modified component of the phosphate backbone, such as phosphorothioate, a phosphorodithioate, a phosphorodiamidate, a phosphoramidate, a phosphordiamidate, a methylphosphonate, an alkyl phosphotriester, or a formacetal or analog thereof.

In an aspect, the invention provides for introduction of an RNA sequence into a transcript recruitment sequence that forms a loop secondary structure and binds to an adapter protein. In an aspect the invention provides a herein-discussed composition, wherein the insertion of distinct RNA sequence(s) that bind to one or more adaptor proteins is an aptamer sequence. In an aspect the invention provides a herein-discussed composition, wherein the aptamer sequence is two or more aptamer sequences specific to the same adaptor protein. In an aspect the invention provides a herein-discussed composition, wherein the aptamer sequence is two or more aptamer sequences specific to a different adaptor protein. In an aspect the invention provides a herein-discussed composition, wherein the adaptor protein comprises MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, PRR1. In an aspect the invention provides a herein-discussed composition, wherein the cell is a eukaryotic cell. In an aspect the invention provides a herein-discussed composition, wherein the eukaryotic cell is a mammalian cell, optionally a mouse cell. In an aspect the invention provides a herein-discussed composition, wherein the mammalian cell is a human cell. Aspects of the invention encompass embodiments relating to MS2 adaptor proteins described in Konermann et al. "Genome-scale transcriptional activation by an engineered CRISPR-Cas9 complex" Nature. 2014 Dec. 10. doi: 10.1038/nature14136, the contents of which are herein incorporated by reference in its entirety.

In some embodiments, the adaptor protein domain is an RNA-binding protein domain. The RNA-binding protein domain recognizes corresponding distinct RNA sequences, which may be aptamers. For example, the MS2 RNA-binding protein recognizes and binds specifically to the MS2 aptamer (or vice versa).

Similarly, an MS2 variant adaptor domain may also be used, such as the N55 mutant, especially the N55K mutant. This is the N55K mutant of the MS2 bacteriophage coat protein (shown to have higher binding affinity than wild type MS2 in Lim, F., M. Spingola, and D. S. Peabody. "Altering the RNA binding specificity of a translational repressor." Journal of Biological Chemistry 269.12 (1994): 9006-9010).

In certain example embodiments, the oligo-nucleotide protein binding molecule may be an aptamer. Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, cells, tissues and organisms. Nucleic acid aptamers have specific binding affinity to molecules through interactions other than classic Watson-Crick base pairing. Aptamers are useful in biotechnological and therapeutic applications as they offer molecular recognition properties similar to antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. In certain embodiments, RNA aptamers may be expressed from a DNA construct. In other embodiments, a nucleic acid aptamer may be linked to another polynucleotide sequence. The polynucleotide sequence may be a double stranded DNA polynucleotide sequence. The aptamer may be covalently linked to one strand of the polynucleotide sequence. The aptamer may be ligated to the polynucleotide sequence. The polynucleotide sequence may be configured, such that the polynucleotide sequence may be linked to a solid support or ligated to another polynucleotide sequence.

Aptamers, like peptides generated by phage display or monoclonal antibodies ("mAbs"), are capable of specifically binding to selected targets and modulating the target's activity, e.g., through binding, aptamers may block their target's ability to function. A typical aptamer is 10-15 kDa in size (30-45 nucleotides), binds its target with sub-nanomolar affinity, and discriminates against closely related targets (e.g., aptamers will typically not bind other proteins from the same gene family). Structural studies have shown that aptamers are capable of using the same types of binding interactions (e.g., hydrogen bonding, electrostatic complementarity, hydrophobic contacts, steric exclusion) that drives affinity and specificity in antibody-antigen complexes.

In certain example embodiments, the protein binding molecule is a lipid or glycolipid. In certain example embodiments, the protein binding molecule is a polysaccharide. Interactions between proteins and polysaccharides may occur via physical bonding such as van der Waals, electrostatic, hydrophobic, hydrogen bonding, and excluded volume effects, or by chemical bonding as in the case of Maillard-type protein-polysaccharide conjugates. The strength and character (net attractive or net repulsive) of protein-polysaccharide non-covalent physical interactions may vary substantially, depending primarily on such environmental conditions as pH, ionic strength, and temperature (Semenova and Dickinson, 2010).

In certain example embodiments, the protein binding molecule is a polypeptide, a whole protein, or a protein binding domain. In certain example embodiments, the polypeptide-based protein binding molecule is an avimer. Avimers are artificial proteins that are able to specifically bind to certain antigens via multiple binding sites. Avimers are not structurally related to antibodies, but are classified as a type of antibody mimetic. Avimers consist of two or more peptide sequences of 30 to 35 amino acids each, connected by linker peptides. The individual sequences are derived from A domains of various membrane receptors and have a rigid structure, stabilized by disulfide bonds and calcium. Each A domain can bind to a certain epitope of the target protein. The combination of domains binding to different epitopes of the same protein increases affinity to this protein, an effect known as avidity. Alternatively, the domains can be directed against epitopes on different target proteins. This approach is similar to the one taken in the development of bispecific monoclonal antibodies. Avimers with two or three domains can bind to their targets in sub-nanomolar concentrations. They have improved heat stability compared with antibodies, but limited plasma half-life because of their smaller size. Half-life can be increased by binding them to antibodies. Domains targeting the desired protein are selected with display techniques such as phage display. The most promising species are linked to a second A domain via a short linker peptide, forming a new library. This process can be repeated several times, yielding avimers with an increasing number of domains.

In certain example embodiments, the polypeptide-based protein binding molecule is an antibody. Antibodies are polypeptide ligands comprising at least a light chain and/or heavy chain immunoglobulin variable region (or fragment thereof) which specifically recognizes and binds an epitope of an antigen, such as a protein, or a fragment thereof. Antibodies can include a heavy and a light chain, each of which has a variable region, termed the variable heavy (VH) region and the variable light (VL) region. The term also includes recombinant forms such as chimeric antibodies (for example, humanized murine antibodies), heteroconjugate antibodies (such as, bispecific antibodies). An antibody or fragment thereof may be multispecific, for example, bispecific. Antibodies include all known forms of antibodies and other protein scaffolds with antibody-like properties. For example, the antibody can be a monoclonal antibody, a polyclonal antibody, human antibody, a humanized antibody, a bispecific antibody, a monovalent antibody, a chimeric antibody, an immunoconjugate, or a protein scaffold with antibody-like properties, such as fibronectin or ankyrin repeats. The antibody can have any of the following isotypes: IgG (for example, IgG1, IgG2, IgG3, and IgG4), IgM, IgA (for example, IgA1, IgA2, and IgAsec), IgD, or IgE.

In most mammals, including humans, whole antibodies have at least two heavy (H) chains and two light (L) chains connected by disulfide bonds. Each heavy chain includes a heavy chain variable region (VH) and a heavy chain constant region (CH). However, single chain VHH variants, such as found in camelids, and fragments thereof, are also included. The heavy chain constant region includes three domains, CH1, CH2, and CH3 and a hinge region between CH1 and CH2. Each light chain includes a light chain variable region (VL) and a light chain constant region. The light chain constant region includes the domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen.

Included are intact immunoglobulins and the variants and portions of them well known in the art, such as Fab fragments, Fab' fragments, F(ab)'2 fragments, single chain Fv proteins ("scFv"), and disulfide stabilized Fv proteins ("dsFv") Fd, Feb, or SMIP. An antibody fragment may be, for example, a diabody, triabody, affibody, nanobody, aptamer, domain antibody, linear antibody, single-chain antibody, or multispecific antibodies formed from antibody fragments. Examples of antibody fragments include: (i) a Fab fragment: a monovalent fragment consisting of VL, VH, CL, and CH1 domains; (ii) a F(ab')2 fragment: a bivalent fragment including two Fab fragments linked by a disulfide bridge at the hinge region; (iii) a Fd fragment: a fragment consisting of VH and CH1 domains; (iv) a Fv fragment: a fragment consisting of the VL and VH domains of a single arm of an antibody; (v) a dAb fragment: a fragment including VH and VL domains; (vi) a dAb fragment: a fragment consisting of a VH domain or a VHH domain (such a Nanobody™); (vii) a dAb fragment: a fragment consisting of a VH or a VL domain; (viii) an isolated complementarity determining region (CDR); and (ix) a combination of two or more isolated CDRs which may optionally be joined by a synthetic linker. Furthermore, although the two domains of the Fv fragment, VL and VH, are coded for by separate genes, they can be joined, using recombinant methods, for example, by a synthetic linker that enables them to be made as a single protein chain in which the VL and VH regions pair to form monovalent molecules (known as single chain Fv (scFv)). Antibody fragments may be obtained using conventional techniques known to those of skill in the art, and may, in some instances, be used in the same manner as intact antibodies. Antigen-binding fragments may be produced by recombinant DNA techniques or by enzymatic or chemical cleavage of intact immunoglobulins. An antibody fragment may further include any of the antibody fragments described above with the addition of additional C-terminal amino acids, N-terminal amino acids, or amino acids separating individual fragments.

An antibody may be referred to as chimeric if it includes one or more variable regions or constant regions derived from a first species and one or more variable regions or constant regions derived from a second species. Chimeric antibodies may be constructed, for example, by genetic engineering. A chimeric antibody may include immunoglobulin gene segments belonging to different species (for example, from a mouse and a human).

A human antibody refers to a specific binding agent having variable regions in which both the framework and CDR regions are derived from human immunoglobulin sequences. Furthermore, if the antibody contains a constant region, the constant region also is derived from a human immunoglobulin sequence. A human antibody may include amino acid residues not identified in a human immunoglobulin sequence, such as one or more sequence variations, for example, mutations. A variation or additional amino acid may be introduced, for example, by human manipulation. A human antibody of the present disclosure is not chimeric.

Antibodies may be humanized, meaning that an antibody that includes one or more complementarity determining regions (for example, at least one CDR) substantially derived from a non-human immunoglobulin or antibody is manipulated to include at least one immunoglobulin domain having a variable region that includes a variable framework region substantially derived from a human immunoglobulin or antibody.

In certain example embodiments, the polypeptide-based protein binding molecule is a protein-binding derivative, or an antibody mimetic, for example. Antibody mimetics can specifically bind antigens, but are not structurally related to antibodies. They are usually artificial peptides or protein with a molar mass of about 3 to 20 kDa. Nucleic acids and small molecules are sometimes considered antibody mimetics as well, but not artificial antibodies, antibody fragments and fusion proteins composed from these. In addition to avimers, described earlier, other examples of antibody mimetics include, but are not necessarily limited to, affibody molecules, affilins, affimers, affitins, alphabodies, anticalins, DARPins, fynomers, Kunitz domain peptides, monobodies, and nanoCLAMPs.

Oligonucleotide Tag

An oligonucleotide tag is attached to the protein binding molecule. The oligonucleotide may function to identify the protein binding molecule and thereby the target polypeptide to be detected using the protein binding molecule, and serve as a means for detection of that target polypeptide through nucleic acid hybridization, amplification, and/or sequencing means, as further defined below. The oligonucleotide tag may be attached to the polypeptide by various linking technologies described in further detail below. The oligonucleotide tag may comprise single stranded RNA, DNA, or combinations thereof. The oligonucleotide tag may comprise double stranded RNA, DNA, or combinations thereof. The oligonucleotide tag may comprise both single-stranded and double-stranded regions. The oligonucleotide tag may comprise, synthetic oligonucleotides in whole or in part. As described earlier, synthetic oligonucleotides include chemically synthesized deoxyribonucleotide or ribonucleotide polymers including without limitation, cDNA, mRNA, genomic DNA, and synthetic DNA or RNA or hybrids thereof. The nucleic acid can be double-stranded (ds) or single-stranded (ss). Where single-stranded, the nucleic acid can be the sense strand or the antisense strand. Nucleic acids can include natural nucleotides (such as A, T/U, C, and G), and can also include analogs of natural nucleotides, such as labeled nucleotides. Some examples of nucleic acids include the probes disclosed herein. The oligonucleotide tag may range from approximately 30 to 300 nucleotides in length.

The oligonucleotide tag may comprise one or more of the following elements; an origin specific barcode, a first primer handle sequence, a second primer handle sequence, a target binding region, and an adapter. These elements may be directly adjacent to another or separated by a spacer sequence. The elements may be ordered in any combination 5' to 3'. In certain example embodiments, the barcode is first. In certain example embodiments, the UMI is first. In certain example embodiments, the barcode and UMI are the first two elements. In certain example embodiments, the barcode is located between the first primer handle sequence and the second primer handle sequence. In certain example embodiments, the barcode and the UMI are located between the first and second primer sequence.

An origin specific barcode is a unique nucleic acid identifier, or a short sequence of nucleotides that can be used as an identifier for an associated molecule, location, or condition. The barcode includes a unique nucleic acid identification sequence that maintains or carries information about the origin of the cell, or acellular system, in the sample. The nucleotide sequence of the origin-specific barcode is detected, thereby assigning the set of target molecules to target nucleic acids in the sample or set of samples while maintaining information about sample origin of the target molecules and the target nucleic acids. In some examples of the method, the target nucleic acids encode the target molecules, such as target polypeptides, for example target proteins. The sequence of the origin-specific barcode, amongst other sequences (such as other nucleic acid barcodes and/or coding sequencing, for example target nucleic acid sequences), can be detected by any method known in the art, such as by amplification, sequencing, hybridization and any combination thereof.

A first primer handle sequence is a nucleotide sequence that may be used, for example, as a forward primer hybridization site for subsequent amplification. A second primer handle sequence is a nucleotide sequence that may be used, for example, as a reverse hybridization site for subsequent amplification. Resulting amplicons generated by amplifying the region between the primer handle sequences may then be sequenced to gain information about target sequence abundance and localization.

The term "target binding region" or "target nucleic acid sequence" or "target DNA or RNA" or "target nucleic acid" or "target oligonucleotide" refers to a protein, or a DNA or RNA polynucleotide being or comprising the target sequence. In other words, the target DNA or RNA may be a DNA or RNA polynucleotide or a part of a DNA or RNA polynucleotide to which a part of the gRNA, i.e. a guide sequence, is designed to have complementarity and to which the effector function mediated by the complex comprising CRISPR effector protein and a gRNA is to be directed. In some embodiments, a target binding region or sequence is located in the nucleus or cytoplasm of a cell.

In some embodiments, the composition may comprise an adapter sequence. The adapter sequence may be an origin-specific barcode receiving adapter, such as a nucleic acid, for example. In some examples, the origin-specific barcode receiving adapter comprises an overhang and the origin-specific barcode comprises a sequence capable of hybridizing to the overhang. A barcode receiving adapter is a molecule configured to accept or receive a nucleic acid barcode, such as an origin-specific nucleic acid barcode. For example, a barcode receiving adapter can include a single-stranded nucleic acid sequence (for example, an overhang) capable of hybridizing to a given barcode (for example, an origin-specific barcode), for example, via a sequence complementary to a portion or the entirety of the nucleic acid barcode. In certain embodiments, this portion of the barcode is a standard sequence held constant between individual barcodes. The hybridization couples the barcode receiving adapter to the barcode. In some embodiments, the barcode receiving adapter may be associated with (for example, attached to) a target molecule. As such, the barcode receiving adapter may serve as the means through which an origin-specific barcode is attached to a target molecule. A barcode receiving adapter can be attached to a target molecule according to methods known in the art. For example, a barcode receiving adapter can be attached to a polypeptide target molecule at a cysteine residue (for example, a C-terminal cysteine residue). A barcode receiving adapter can be used to identify a particular condition related to one or more target molecules, such as a cell of origin or a discreet volume of origin. For example, a target molecule can be a cell surface protein expressed by a cell, which receives a cell-specific barcode receiving adapter. The barcode receiving adapter can be conjugated to one or more barcodes as the cell is exposed to one or more conditions, such that the original cell of origin for the target molecule, as well as each condition to which the cell was exposed, can be subsequently determined by identifying the sequence of the barcode receiving adapter/barcode concatemer.

In some embodiments, the oligonucleotide may further comprise a unique molecular identifier (UMI). The term "unique molecular identifiers" (UMI) as used herein refers to a sequencing linker or a subtype of nucleic acid barcode used in a method that uses molecular tags to detect and quantify unique amplified products. A UMI is used to distinguish effects through a single clone from multiple clones. The term "clone" as used herein may refer to a single mRNA or target nucleic acid to be sequenced. The UMI may also be used to determine the number of transcripts that gave rise to an amplified product, or in the case of target barcodes as described herein, the number of binding events. In preferred embodiments, the amplification is by PCR or multiple displacement amplification (MDA).

In certain embodiments, an UMI with a random sequence of between 4 and 20 base pairs is added to a template, which is amplified and sequenced. In preferred embodiments, the UMI is added to the 5' end of the template. Sequencing allows for high resolution reads, enabling accurate detection of true variants. As used herein, a "true variant" will be present in every amplified product originating from the original clone as identified by aligning all products with a UMI. Each clone amplified will have a different random UMI that will indicate that the amplified product originated from that clone. Background caused by the fidelity of the amplification process can be eliminated because true variants will be present in all amplified products and background representing random error will only be present in single amplification products (See e.g., Islam S. et al., 2014. Nature Methods No: 11, 163-166). Not being bound by a theory, the UMI's are designed such that assignment to the original can take place despite up to 4-7 errors during amplification or sequencing. Not being bound by a theory, an UMI may be used to discriminate between true barcode sequences.

Unique molecular identifiers can be used, for example, to normalize samples for variable amplification efficiency. For example, in various embodiments, featuring a solid or semisolid support (for example a hydrogel bead), to which nucleic acid barcodes (for example a plurality of barcodes sharing the same sequence) are attached, each of the barcodes may be further coupled to a unique molecular identifier, such that every barcode on the particular solid or semisolid support receives a distinct unique molecule identifier. A unique molecular identifier can then be, for example, transferred to a target molecule with the associated barcode, such that the target molecule receives not only a nucleic acid barcode, but also an identifier unique among the identifiers originating from that solid or semisolid support.

A nucleic acid barcode or UMI can have a length of at least, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 nucleotides, and can be in single- or double-stranded form. Target molecule and/or target nucleic acids can be labeled with multiple nucleic acid barcodes in combinatorial fashion, such as a nucleic acid barcode concatemer. Typically, a nucleic acid barcode is used to identify a target molecule and/or target nucleic acid as being from a particular discrete volume, having a particular physical property (for example, affinity, length, sequence, etc.), or having been subject to certain treatment conditions. Target molecule and/or target nucleic acid can be associated with multiple nucleic acid barcodes to provide information about all of these features (and more). Each member of a given population of UMIs, on the other hand, is typically associated with (for example, covalently bound to or a component of the same molecule as) individual members of a particular set of identical, specific (for example, discreet volume-, physical property-, or treatment condition-specific) nucleic acid barcodes. Thus, for example, each member of a set of origin-specific nucleic acid barcodes, or other nucleic acid identifier or connector oligonucleotide, having identical or matched barcode sequences, may be associated with (for example, covalently bound to or a component of the same molecule as) a distinct or different UMI.

The origin specific barcode, first primer handle sequence, second primer handle sequence, targeting binding region, and adapter elements may be directly adjacent to another or separated by a spacer sequence. A spacer sequence may be a cleavable linker, such as a photocleavable linker, such that it may be cleaved upon application of a suitable stimulus. For example, the cleavable sequence may be a photocleavable linker that can be cleaved by applying light or a cleavable linker that can be cleaved by applying a suitable chemical or enzyme.

The term "primer" as used herein refers to short nucleic acid molecules, such as a DNA oligonucleotide, for example sequences of at least 15 nucleotides, which can be annealed to a complementary nucleic acid molecule by nucleic acid hybridization to form a hybrid between the primer and the nucleic acid strand. A primer can be extended along the nucleic acid molecule by a polymerase enzyme. Therefore, primers can be used to amplify a nucleic acid molecule, wherein the sequence of the primer is specific for the nucleic acid molecule, for example so that the primer will hybridize to the nucleic acid molecule under very high stringency hybridization conditions. The specificity of a primer increases with its length. Thus, for example, a primer that includes 30 consecutive nucleotides will anneal to a sequence with a higher specificity than a corresponding primer of only 15 nucleotides. Thus, to obtain greater specificity, probes and primers can be selected that include at least 15, 20, 25, 30, 35, 40, 45, 50 or more consecutive nucleotides.

In particular examples, a primer is at least 15 nucleotides in length, such as at least 15 contiguous nucleotides complementary to a nucleic acid molecule. Particular lengths of primers that can be used to practice the methods of the present disclosure, include primers having at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, or more contiguous nucleotides complementary to the target nucleic acid molecule to be amplified, such as a primer of 15-60 nucleotides, 15-50 nucleotides, or 15-30 nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction. PCR primer pairs can be derived from a known sequence, for example, by using computer programs intended for that purpose such as Primer (Version 0.5, © 1991, Whitehead Institute for Biomedical Research, Cambridge, Mass.).

Methods for preparing and using primers are described in, for example, Sambrook et al. (1989) Molecular Cloning: A Laboratory Manual, Cold Spring Harbor, N.Y.; Ausubel et al. (1987) Current Protocols in Molecular Biology, Greene Publ. Assoc. & Wiley-Intersciences. In one example, a primer includes a label.

Probes are isolated nucleic acids capable of hybridizing to a specific nucleic acid (such as a nucleic acid barcode or target nucleic acid). A detectable label or reporter molecule can be attached to a probe. Typical labels include radioactive isotopes, enzyme substrates, co-factors, ligands, chemiluminescent or fluorescent agents, haptens, and enzymes. In some example, a probe is used to isolate and/or detect a specific nucleic acid.

Methods for labeling and guidance in the choice of labels appropriate for various purposes are discussed, for example, in Sambrook et al., Molecular Cloning: A Laboratory Manual, Cold Spring Harbor Laboratory Press (1989) and Ausubel et al., Current Protocols in Molecular Biology, Greene Publishing Associates and Wiley-Intersciences (1987).

Probes are generally about 15 nucleotides in length to about 160 nucleotides in length, such as 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 contiguous nucleotides complementary to the specific nucleic acid molecule, such as 50-140 nucleotides, 75-150 nucleotides, 60-70 nucleotides, 30-130 nucleotides, 20-60 nucleotides, 20-50 nucleotides, 20-40 nucleotides, or 20-30 nucleotides.

The term "barcode" as used herein refers to a short sequence of nucleotides (for example, DNA or RNA) that is used as an identifier for an associated molecule, such as a target molecule and/or target nucleic acid, or as an identifier of the source of an associated molecule, such as a cell-of-origin. A barcode may also refer to any unique, non-naturally occurring, nucleic acid sequence that may be used to identify the originating source of a nucleic acid fragment. Although it is not necessary to understand the mechanism of an invention, it is believed that the barcode sequence provides a high-quality individual read of a barcode associated with a single cell, a viral vector, labeling ligand (e.g., an aptamer), protein, shRNA, sgRNA or cDNA such that multiple species can be sequenced together.

In certain embodiments, nucleic acids comprise non-naturally occurring nucleic acids and/or non-naturally occurring nucleotides and/or nucleotide analogs, and/or chemical modifications. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a nucleic acid comprises ribonucleotides and non-ribonucleotides. In one such embodiment, a nucleic acid comprises one or more ribonucleotides and one or more deoxyribonucleotides. In an embodiment of the invention, the nucleic acid comprises one or more non-naturally occurring nucleotide or nucleotide analog such as a nucleotide with phosphorothioate linkage, boranophosphate linkage, a locked nucleic acid (LNA) nucleotides comprising a methylene bridge between the 2' and 4' carbons of the ribose ring, peptide nucleic acids (PNA), or bridged nucleic acids (BNA). Other examples of modified nucleotides include 2'-O-methyl analogs, 2'-deoxy analogs, 2-thiouridine analogs, N6-methyladenosine analogs, or 2'-fluoro analogs. Further examples of modified nucleotides include linkage of chemical moieties at the 2' position, including but not limited to peptides, nuclear localization sequence (NLS), peptide nucleic acid (PNA), polyethylene glycol (PEG), triethylene glycol, or tetraethyleneglycol (TEG). Further examples of modified bases include, but are not limited to, 2-aminopurine, 5-bromo-uridine, pseudouridine (Ψ), N1-methylpseudouridine (mel Ψ), 5-methoxyuridine (5moU), inosine, 7-methylguanosine. Examples of RNA chemical modifications include, without limitation, incorporation of 2'-O-methyl (M), 2'-O-methyl-3'-phosphorothioate (MS), phosphorothioate (PS), S-constrained ethyl(cEt), 2'-O-methyl-3'-thioPACE (MSP), or 2'-O-methyl-3'-phosphonoacetate (MP) at one or more terminal nucleotides. Such chemically modified RNAs can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015; Ragdarm et al., 0215, PNAS, E7110-E7111; Allerson et al., J. Med. Chem. 2005, 48:901-904; Bramsen et al., Front. Genet., 2012, 3:154; Deng et al., PNAS, 2015, 112:11870-11875; Sharma et al., MedChemComm., 2014, 5:1454-1471; Hendel et al., Nat. Biotechnol. (2015) 33(9): 985-989; Li et al., Nature Biomedical Engineering, 2017, 1, 0066 DOI:10.1038/s41551-017-0066; Ryan et al., Nucleic Acids Res. (2018) 46(2): 792-803).

Barcoding may be performed based on any of the compositions or methods disclosed in patent publication WO 2014047561 A1, Compositions and methods for labeling of agents, incorporated herein in its entirety. In certain embodiments barcoding uses an error correcting scheme (T. K. Moon, Error Correction Coding: Mathematical Methods and Algorithms (Wiley, New York, ed. 1, 2005)). Not being bound by a theory, amplified sequences from single cells can be sequenced together and resolved based on the barcode associated with each cell.

As disclosed herein, unique nucleic acid identifiers are used to label the target molecules and/or target nucleic acids, for example origin-specific barcodes and the like. The nucleic acid identifiers, nucleic acid barcodes, can include a short sequence of nucleotides that can be used as an identifier for an associated molecule, location, or condition. In certain embodiments, the nucleic acid identifier further includes one or more unique molecular identifiers and/or barcode receiving adapters. A nucleic acid identifier can have a length of about, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 base pairs (bp) or nucleotides (nt). In certain embodiments, a nucleic acid identifier can be constructed in combinatorial fashion by combining randomly selected indices (for example, about 1, 2, 3, 4, 5, 6, 7, 8, 9, or 10 indexes). Each such index is a short sequence of nucleotides (for example, DNA, RNA, or a combination thereof) having a distinct sequence. An index can have a length of about, for example, 4, 5, 6, 7, 8, 9, 10, 11, 12, 13, 14, 15, 16, 17, 18, 19, 20, 21, 22, 23, 24, or 25 bp or nt. Nucleic acid identifiers can be generated, for example, by split-pool synthesis methods, such as those described, for example, in International Patent Publication Nos. WO 2014/047556 and WO 2014/143158, each of which is incorporated by reference herein in its entirety.

One or more nucleic acid identifiers (for example a nucleic acid barcode) can be attached, or "tagged," to a target molecule. This attachment can be direct (for example, covalent or noncovalent binding of the nucleic acid identifier to the target molecule) or indirect (for example, via an additional molecule). Such indirect attachments may, for example, include a barcode bound to a specific-binding agent that recognizes a target molecule. In certain embodiments, a barcode is attached to protein G and the target molecule is an antibody or antibody fragment. Attachment of a barcode to target molecules (for example, proteins and other biomolecules) can be performed using standard methods well known in the art. For example, barcodes can be linked via cysteine residues (for example, C-terminal cysteine residues). In other examples, barcodes can be chemically introduced into polypeptides (for example, antibodies) via a variety of functional groups on the polypeptide using appropriate group-specific reagents (see for example www-.drmr.com/abcon). In certain embodiments, barcode tagging can occur via a barcode receiving adapter associate with (for example, attached to) a target molecule, as described herein.

Target molecules can be optionally labeled with multiple barcodes in combinatorial fashion (for example, using multiple barcodes bound to one or more specific binding agents that specifically recognizing the target molecule), thus greatly expanding the number of unique identifiers possible within a particular barcode pool. In certain embodiments, barcodes are added to a growing barcode concatemer attached to a target molecule, for example, one at a time. In other embodiments, multiple barcodes are assembled prior to attachment to a target molecule. Compositions and methods for concatemerization of multiple barcodes are described, for example, in International Patent Publication No. WO 2014/047561, which is incorporated herein by reference in its entirety.

In some embodiments, a nucleic acid identifier (for example, a nucleic acid barcode) may be attached to sequences that allow for amplification and sequencing (for example, SBS3 and P5 elements for Illumina sequencing). In certain embodiments, a nucleic acid barcode can further include a hybridization site for a primer (for example, a single-stranded DNA primer) attached to the end of the barcode. For example, an origin-specific barcode may be a nucleic acid including a barcode and a hybridization site for a specific primer. In particular embodiments, a set of origin-specific barcodes includes a unique primer specific barcode made, for example, using a randomized oligo type NNNNNNNNNNNN (SEQ ID NO:4).

A nucleic acid identifier can further include a unique molecular identifier and/or additional barcodes specific to, for example, a common support to which one or more of the nucleic acid identifiers are attached. Thus, a pool of target molecules can be added, for example, to a discrete volume containing multiple solid or semisolid supports (for example, beads) representing distinct treatment conditions (and/or, for example, one or more additional solid or semisolid support can be added to the discreet volume sequentially after introduction of the target molecule pool), such that the precise combination of conditions to which a given target molecule was exposed can be subsequently determined by sequencing the unique molecular identifiers associated with it.

Labeled target molecules and/or target nucleic acids associated origin-specific nucleic acid barcodes (optionally in combination with other nucleic acid barcodes as described herein) can be amplified by methods known in the art, such as polymerase chain reaction (PCR). For example, the nucleic acid barcode can contain universal primer recognition sequences that can be bound by a PCR primer for PCR amplification and subsequent high-throughput sequencing. In certain embodiments, the nucleic acid barcode includes or is linked to sequencing adapters (for example, universal primer recognition sequences) such that the barcode and sequencing adapter elements are both coupled to the target molecule. In particular examples, the sequence of the origin specific barcode is amplified, for example using PCR. In some embodiments, an origin-specific barcode further comprises a sequencing adaptor. In some embodiments, an origin-specific barcode further comprises universal priming sites. A nucleic acid barcode (or a concatemer thereof), a target nucleic acid molecule (for example, a DNA or RNA molecule), a nucleic acid encoding a target peptide or polypeptide, and/or a nucleic acid encoding a specific binding agent may be optionally sequenced by any method known in the art, for example, methods of high-throughput sequencing, also known as next generation sequencing or deep sequencing. A nucleic acid target molecule labeled with a barcode (for example, an origin-specific barcode) can be sequenced with the barcode to produce a single read and/or contig containing the sequence, or portions thereof, of both the target molecule and the barcode. Exemplary next generation sequencing technologies include, for example, Illumina sequencing, Ion Torrent sequencing, 454 sequencing, SOLiD sequencing, and nanopore sequencing amongst others. In some embodiments, the sequence of labeled target molecules is determined by non-sequencing based methods.

For example, variable length probes or primers can be used to distinguish barcodes (for example, origin-specific barcodes) labeling distinct target molecules by, for example, the length of the barcodes, the length of target nucleic acids, or the length of nucleic acids encoding target polypeptides. In other instances, barcodes can include sequences identifying, for example, the type of molecule for a particular target molecule (for example, polypeptide, nucleic acid, small molecule, or lipid). For example, in a pool of labeled target molecules containing multiple types of target molecules, polypeptide target molecules can receive one identifying sequence, while target nucleic acid molecules can receive a different identifying sequence. Such identifying sequences can be used to selectively amplify barcodes labeling particular types of target molecules, for example, by using PCR primers specific to identifying sequences specific to particular types of target molecules. For example, barcodes labeling polypeptide target molecules can be selectively amplified from a pool, thereby retrieving only the barcodes from the polypeptide subset of the target molecule pool.

A nucleic acid barcode can be sequenced, for example, after cleavage, to determine the presence, quantity, or other feature of the target molecule. In certain embodiments, a nucleic acid barcode can be further attached to a further nucleic acid barcode. For example, a nucleic acid barcode can be cleaved from a specific-binding agent after the specific-binding agent binds to a target molecule or a tag (for example, an encoded polypeptide identifier element cleaved from a target molecule), and then the nucleic acid barcode can be ligated to an origin-specific barcode. The resultant nucleic acid barcode concatemer can be pooled with other such concatemers and sequenced. The sequencing reads can be used to identify which target molecules were originally present in which discrete volumes.

DNA barcoding is also a taxonomic method that uses a short genetic marker in an organism's DNA to identify it as belonging to a particular species. It differs from molecular phylogeny in that the main goal is not to determine classification but to identify an unknown sample in terms of a known classification. Kress et al., "Use of DNA barcodes to identify flowering plants" Proc. Natl. Acad. Sci. U.S.A. 102(23):8369-8374 (2005). Barcodes are sometimes used in an effort to identify unknown species or assess whether species should be combined or separated. Koch H., "Combining morphology and DNA barcoding resolves the taxonomy of Western Malagasy Liotrigona Moure, 1961" African Invertebrates 51(2): 413-421 (2010); and Seberg et al., "How many loci does it take to DNA barcode a crocus?" PLoS One 4(2):e4598 (2009). Barcoding has been used, for example, for identifying plant leaves even when flowers or fruit are not available, identifying the diet of an animal based on stomach contents or feces, and/or identifying products in commerce (for example, herbal supplements or wood). Soininen et al., "Analysing diet of small herbivores: the efficiency of DNA barcoding coupled with high-throughput pyrosequencing for deciphering the composition of complex plant mixtures" Frontiers in Zoology 6:16 (2009).

It has been suggested that a desirable locus for DNA barcoding should be standardized so that large databases of sequences for that locus can be developed. Most of the taxa of interest have loci that are sequencable without species-specific PCR primers. CBOL Plant Working Group, "A DNA barcode for land plants" PNAS 106(31):12794-12797 (2009). Further, these putative barcode loci are believed short enough to be easily sequenced with current technology. Kress et al., "DNA barcodes: Genes, genomics, and bioinformatics" PNAS 105(8):2761-2762 (2008). Consequently, these loci would provide a large variation between species in combination with a relatively small amount of variation within a species. Lahaye et al., "DNA barcoding the floras of biodiversity hotspots" Proc Natl Acad Sci USA 105(8): 2923-2928 (2008).

DNA barcoding is based on a relatively simple concept. For example, most eukaryote cells contain mitochondria, and mitochondrial DNA (mtDNA) has a relatively fast mutation rate, which results in significant variation in mtDNA sequences between species and, in principle, a comparatively small variance within species. A 648-bp region of the mitochondrial cytochrome c oxidase subunit 1 (CO1) gene was proposed as a potential 'barcode'. As of 2009, databases of CO1 sequences included at least 620,000 specimens from over 58,000 species of animals, larger than databases available for any other gene. Ausubel, J., "A botanical macroscope" Proceedings of the National Academy of Sciences 106(31): 12569 (2009).

Software for DNA barcoding requires integration of a field information management system (FIMS), laboratory information management system (LIMS), sequence analysis tools, workflow tracking to connect field data and laboratory data, database submission tools and pipeline automation for scaling up to eco-system scale projects. Geneious Pro can be used for the sequence analysis components, and the two plugins made freely available through the Moorea Biocode Project, the Biocode LIMS and Genbank Submission plugins handle integration with the FIMS, the LIMS, workflow tracking and database submission.

Additionally, other barcoding designs and tools have been described (see e.g., Birrell et al., (2001) Proc. Natl Acad. Sci. USA 98, 12608-12613; Giaever, et al., (2002) Nature 418, 387-391; Winzeler et al., (1999) Science 285, 901-906; and Xu et al., (2009) Proc Natl Acad Sci USA. February 17; 106(7):2289-94).

In some embodiments, the oligonucleotide may comprise single-stranded RNA. In some embodiments, the oligonucleotide may comprise single-stranded or double-stranded DNA or a synthetic oligonucleotide. In some embodiments, the oligonucleotide may further comprise a poly-A sequence.

In specific embodiments, the first primer handle sequence may be CACCCGAGAATTCCA (SEQ ID NO:1) and the second primer handle sequence may be CTCGATAGCC (SEQ ID NO:2).

Methods for Simultaneously Measuring Protein and Target Oligonucleotides in Single Cells Also provided within the scope of the invention, are methods for simultaneously measuring target oligonucleotides and protein in single cells. Such methods may comprise delivering a mixture of any of the compositions provided herein to a population of cells. As such, individual cells may be encapsulated in an individual discrete volume as described herein. In some embodiments, the individual discrete volume may be a hydrogel droplet. The individual discrete volume may comprise PCR primers on a bead as described herein. The individual discrete volume may be suspended in a reverse transcription mixture and the nucleotide sequence of the origin specific barcode sequence may be detected. This allows one to assign the target oligonucleotide and protein of interest to a specific individual discrete volume, and maintain information about sample origin of the target oligonucleotide.

In some embodiments, the cells or population of cells may be obtained from a biological sample. The biological sample may be obtained from a subject suffering from a disease. The biological sample may be a tumor sample. The tumor may be any tumor. This may include, without limitation, liquid tumors such as leukemia (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease, non-Hodgkin's disease), Waldenstrom's macroglobulinemia, heavy chain disease, or multiple myeloma.

In some embodiments, the target molecule or sequence may be associated with diseased cells or a disease state. For instance, a target molecule may be associated with cancer cells, for example, a protein, polypeptide, or nucleic acid selectively expressed or not expressed by cancer cells, or may specifically bind to such a protein or polypeptide (for example, an antibody or fragment thereof, for example, as described herein). In certain instances, the target molecule is a tumor marker, for example, a substance produced by a tumor or produced by a non-cancer cell (for example, a stromal cell) in response to the presence of a tumor. Many tumor markers are not exclusively expressed by cancer cells, but may be expressed at altered (i.e., elevated or decreased) levels in cancerous cells or expressed at altered (i.e., elevated or decreased) levels in non-cancer cells in response to the presence of a tumor. In some embodiments, the target molecule may be a protein, polypeptide, or nucleic acid expressed in connection with any disease or condition known in the art.

The tumor may also include, without limitation, solid tumors such as sarcomas and carcinomas. Examples of solid tumors include, but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, epithelial carcinoma, bronchogenic carcinoma, hepatoma, colorectal cancer (e.g., colon cancer, rectal cancer), anal cancer, pancreatic cancer (e.g., pancreatic adenocarcinoma, islet cell carcinoma, neuroendocrine tumors), breast cancer (e.g., ductal carcinoma, lobular carcinoma, inflammatory breast cancer, clear cell carcinoma, mucinous carcinoma), ovarian carcinoma (e.g., ovarian epithelial carcinoma or surface epithelial-stromal tumour including serous tumour, endometrioid tumor and mucinous cystadenocarcinoma, sex-cord-stromal tumor), prostate cancer, liver and bile duct carcinoma (e.g., hepatocellular carcinoma, cholangiocarcinoma, hemangioma), choriocarcinoma, seminoma, embryonal carcinoma, kidney cancer (e.g., renal cell carcinoma, clear cell carcinoma, Wilm's tumor, nephroblastoma), cervical cancer, uterine cancer (e.g., endometrial adenocarcinoma, uterine papillary serous carcinoma, uterine clear-cell carcinoma, uterine sarcomas and leiomyosarcomas, mixed mullerian tumors), testicular cancer, germ cell tumor, lung cancer (e.g., lung adenocarcinoma, squamous cell carcinoma, large cell carcinoma, bronchioloalveolar carcinoma, non-small-cell carcinoma, small cell carcinoma, mesothelioma), bladder carcinoma, signet ring cell carcinoma, cancer of the head and neck (e.g., squamous cell carcinomas), esophageal carcinoma (e.g., esophageal adenocarcinoma), tumors of the brain (e.g., glioma, glioblastoma, medulloblastoma, astrocytoma, medulloblastoma, craniopharyngioma, ependymoma, pinealoma, hemangioblastoma, acoustic neuroma, oligodendroglioma, schwannoma, meningioma), neuroblastoma, retinoblastoma, neuroendocrine tumor, melanoma, cancer of the stomach (e.g., stomach adenocarcinoma, gastrointestinal stromal tumor), or carcinoids. Lymphoproliferative disorders are also considered to be proliferative diseases.

Individual cells may be encapsulated in an individual discrete volume, which may include PCR primers on a bead. An "individual discrete volume" is a discrete volume or discrete space, such as a container, receptacle, or other defined volume or space that can be defined by properties that prevent and/or inhibit migration of nucleic acids and reagents necessary to carry out the methods disclosed herein, for example a volume or space defined by physical properties such as walls, for example the walls of a well, tube, or a surface of a droplet, which may be impermeable or semipermeable, or as defined by other means such as chemical, diffusion rate limited, electro-magnetic, or light illumination, or any combination thereof. By "diffusion rate limited" (for example diffusion defined volumes) is meant spaces that are only accessible to certain molecules or reactions because diffusion constraints effectively defining a space or volume as would be the case for two parallel laminar streams where diffusion will limit the migration of a target molecule from one stream to the other. By "chemical" defined volume or space is meant spaces where only certain target molecules can exist because of their chemical or molecular properties, such as size, where for example gel beads may exclude certain species from entering the beads but not others, such as by surface charge, matrix size or other physical property of the bead that can allow selection of species that may enter the interior of the bead. By "electro-magnetically" defined volume or space is meant spaces where the electro-magnetic properties of the target molecules or their supports such as charge or magnetic properties can be used to define certain regions in a space such as capturing magnetic particles within a magnetic field or directly on magnets. By "optically" defined volume is meant any region of space that may be defined by illuminating it with visible, ultraviolet, infrared, or other wavelengths of light such that only target molecules within the defined space or volume may be labeled. One advantage to the used of non-walled, or semipermeable is that some reagents, such as buffers, chemical activators, or other agents maybe passed in our through the discrete volume, while other material, such as target molecules, maybe maintained in the discrete volume or space. Typically, a discrete volume will include a fluid medium, (for example, an aqueous solution, an oil, a buffer, and/or a media capable of supporting cell growth) suitable for labeling of the target molecule with the indexable nucleic acid identifier under conditions that permit labeling. Exemplary discrete volumes or spaces useful in the disclosed methods include droplets (for example, microfluidic droplets and/or emulsion droplets), hydrogel beads or other polymer structures (for example poly-ethylene glycol di-acrylate beads or agarose beads), tissue slides (for example, fixed formalin paraffin embedded tissue slides with particular regions, volumes, or spaces defined by chemical, optical, or physical means), microscope slides with regions defined by depositing reagents in ordered arrays or random patterns, tubes (such as, centrifuge tubes, microcentrifuge tubes, test tubes, cuvettes, conical tubes, and the like), bottles (such as glass bottles, plastic bottles, ceramic bottles, Erlenmeyer flasks, scintillation vials and the like), wells (such as wells in a plate), plates, pipettes, or pipette tips among others. In certain example embodiments, the individual discrete volumes are the wells of a microplate. In certain example embodiments, the microplate is a 96 well, a 384 well, or a 1536 well microplate.

In specific embodiments, the individual discrete volume may be a hydrogel droplet. The individual discrete volume may then be resuspended in a reverse transcription mixture and the nucleotide sequence of the origin specific barcode handle sequence may be detected, thereby assigning the target oligonucleotide and protein of interest to a specific individual discrete volume, while maintaining information about sample origin of the target oligonucleotide. As described elsewhere herein, the protein binding molecule may be an antibody, but is not necessarily limited thereto.

In some embodiments, detection of the nucleotide sequence of the origin specific barcode handle sequence may be achieved by nucleic acid sequencing, amplification, hybridization, or any combination thereof.

Nucleic acid sequencing is the process of determining the nucleotide order of a given DNA molecule. Generally, the sequencing can be performed using automated Sanger sequencing (AB13730xl genome analyzer), pyrosequencing on a solid support (454 sequencing, Roche), sequencing-by-synthesis with reversible terminations (ILLUMINA® Genome Analyzer), sequencing-by-ligation (ABI SOLiD®) or sequencing-by-synthesis with virtual terminators (HELISCOPE®). In some embodiments, the identity of a nucleic acid is determined by DNA or RNA sequencing. Generally, the sequencing can be performed using automated Sanger sequencing (AB13730xl genome analyzer), pyrosequencing on a solid support (454 sequencing, Roche), sequencing-by-synthesis with reversible terminations (ILLUMINA® Genome Analyzer), sequencing-by-ligation (ABI SOLiD®) or sequencing-by-synthesis with virtual terminators (HELISCOPE®); Moleculo sequencing (see Voskoboynik et al. eLife 2013 2:e00569 and U.S. patent application Ser. No. 13/608,778, filed Sep. 10, 2012); DNA nanoball sequencing; Single molecule real time (SMRT) sequencing; Nanopore DNA sequencing; Sequencing by hybridization; Sequencing with mass spectrometry; and Microfluidic Sanger sequencing.

In some embodiments, DNA sequencing is performed using a chain termination method developed by Frederick Sanger, and thus termed "Sanger based sequencing" or "SBS." This technique uses sequence-specific termination of a DNA synthesis reaction using modified nucleotide substrates. Extension is initiated at a specific site on the template DNA by using a short oligonucleotide primer complementary to the template at that region. The oligonucleotide primer is extended using DNA polymerase in the presence of the four deoxynucleotide bases (DNA building blocks), along with a low concentration of a chain terminating nucleotide (most commonly a di-deoxynucleotide). Limited incorporation of the chain terminating nucleotide by the DNA polymerase results in a series of related DNA fragments that are terminated only at positions where that particular nucleotide is present. The fragments are then size-separated by electrophoresis a polyacrylamide gel, or in a narrow glass tube (capillary) filled with a viscous polymer. An alternative to using a labeled primer is to use labeled terminators instead; this method is commonly called "dye terminator sequencing."

"Pyrosequencing" is an array based method, which has been commercialized by 454 Life Sciences. In some embodiments of the array-based methods, single-stranded DNA is annealed to beads and amplified via EmPCR®. These DNA-bound beads are then placed into wells on a fiber-optic chip along with enzymes that produce light in the presence of ATP. When free nucleotides are washed over this chip, light is produced as the PCR amplification occurs and ATP is generated when nucleotides join with their complementary base pairs. Addition of one (or more) nucleotide(s) results in a reaction that generates a light signal that is recorded, such as by the charge coupled device (CCD) camera, within the instrument. The signal strength is proportional to the number of nucleotides, for example, homopolymer stretches, incorporated in a single nucleotide flow.

In certain embodiments, the invention involves high-throughput single-cell RNA-seq and/or targeted nucleic acid profiling (for example, sequencing, quantitative reverse transcription polymerase chain reaction, and the like) where the RNAs from different cells are tagged individually, allowing a single library to be created while retaining the cell identity of each read. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO 2014210353 A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; and Rosenberg et al., 2017, "Scaling single cell transcriptomics through split pool barcoding" bioRxiv preprint first posted online Feb. 2, 2017, doi: dx.doi.org/10.1101/105163, all the contents and disclosure of each of which are herein incorporated by reference in their entirety.

In certain embodiments, the invention involves plate based single cell RNA sequencing (see, e.g., Picelli, S. et al., 2014, "Full-length RNA-seq from single cells using Smart-seq2" Nature protocols 9, 171-181, doi: 10.1038/nprot.2014.006).

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 Oct.; 14(10):955-958; and International patent application number PCT/US2016/059239, published as WO2017164936 on Sep. 28, 2017, which are herein incorporated by reference in their entirety.

The term "tagmentation" refers to a step in the Assay for Transposase Accessible Chromatin using sequencing (ATAC-seq) as described. (See, Buenrostro, J. D., Giresi, P. G., Zaba, L. C., Chang, H. Y., Greenleaf, W. J., Transposition of native chromatin for fast and sensitive epigenomic profiling of open chromatin, DNA-binding proteins and nucleosome position. Nature methods 2013; 10 (12): 1213-1218). Specifically, a hyperactive Tn5 transposase loaded in vitro with adapters for high-throughput DNA sequencing, can simultaneously fragment and tag a genome with sequencing adapters. In one embodiment the adapters are compatible with the methods described herein.

In certain embodiments, tagmentation is used to introduce adaptor sequences to genomic DNA in regions of accessible chromatin (e.g., between individual nucleosomes) (see, e.g., US20160208323A1; US20160060691A1; WO2017156336A1; and Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. Science. 2015 May 22; 348(6237):910-4. doi: 10.1126/science.aab1601. Epub 2015 May 7). In certain embodiments, tagmentation is applied to bulk samples or to single cells in discrete volumes.

One embodiment of the invention may comprise amplifying the target nucleic acid sequence. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include quantitative real-time PCR; reverse transcriptase PCR (RT-PCR); real-time PCR (rt PCR); real-time reverse transcriptase PCR (rt RT-PCR); nested PCR; strand displacement amplification (see U.S. Pat. No. 5,744,311); transcription-free isothermal amplification (see U.S. Pat. No. 6,033,881, repair chain reaction amplification (see WO 90/01069); ligase chain reaction amplification (see European patent publication EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134) amongst others.

The amplification can be isothermal and selected for temperature. In one embodiment, the amplification proceeds rapidly at 37 degrees. In other embodiments, the temperature of the isothermal amplification may be chosen by selecting a polymerase operable at a different temperature. The polymerase can be selected from the group consisting of Bst 2.0 DNA polymerase, Bst 2.0 WarmStart DNA polymerase, Bst 3.0 DNA polymerase, full length Bst DNA polymerase, large fragment Bst DNA polymerase, large fragment Bsu DNA polymerase, phi29 DNA polymerase, T7 DNA polymerase, and Sequenase DNA polymerase. In specific embodiments, amplification of the target nucleic acid sequence is performed at a constant temperature.

The amplification can be used to amplify target nucleic acid sequences with varying lengths. For example, the target nucleic acid sequence can be about 10-20, about 20-30, about 30-40, about 40-50, about 50-100, about 100-200, about 100-200, about 100-1000, about 1000-2000, about 2000-3000, about 3000-4000, or about 4000-5000 nucleotides in length. The target nucleic acid can be DNA, for example, genomic DNA, mitochondrial DNA, viral DNA, plasmid DNA, or synthetic double-stranded DNA. The target nucleic acid can be single-stranded nucleic acid, for example, an RNA molecule. The single-stranded nucleic acid can be converted to a double-stranded nucleic acid prior to based amplification. For example, an RNA molecule can be converted to a double-stranded DNA by reverse transcription prior to amplification. The single-stranded nucleic acid can be selected from the group consisting of single-stranded viral DNA, viral RNA, messenger RNA, ribosomal RNA, transfer RNA, microRNA, short interfering RNA, small nuclear RNA, synthetic RNA, and synthetic single-stranded DNA.

The isothermal amplification method can be combined with a variety of detection methods to detect the amplified nucleic acid products. For example, the detection methods can comprise gel electrophoresis, intercalating dye detection, PCR, real-time PCR, fluorescence, Fluorescence Resonance Energy Transfer (FRET), mass spectrometry, real-time RPA, real-time LAMP, real-time NEAR, real-time HDA, real-time transcription-mediated amplification (TMA), real-time NASBA, and CRISPR-SHERLOCK. The combined amplification and detection can achieve attomolar sensitivity or femtomolar sensitivity.

The amplification method can include, but is not necessarily limited to, nucleic-acid sequenced-based amplification (NASBA), recombinase polymerase amplification (RPA), loop-mediated isothermal amplification (LAMP), strand displacement amplification (SDA), helicase-dependent amplification (HDA), or nicking enzyme amplification reaction (NEAR).

Accordingly, in certain example embodiments the systems disclosed herein may include amplification reagents. Different components or reagents useful for amplification of nucleic acids are described herein. For example, an amplification reagent as described herein may include a buffer, such as a Tris buffer. A Tris buffer may be used at any concentration appropriate for the desired application or use, for example including, but not limited to, a concentration of 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 25 mM, 50 mM, 75 mM, 1 M, or the like. One of skill in the art will be able to determine an appropriate concentration of a buffer such as Tris for use with the present invention.

A salt, such as magnesium chloride (MgCl2), potassium chloride (KCl), or sodium chloride (NaCl), may be included in an amplification reaction, such as PCR, in order to improve the amplification of nucleic acid fragments. Although the salt concentration will depend on the particular reaction and application, in some embodiments, nucleic acid fragments of a particular size may produce optimum results at particular salt concentrations. Larger products may require altered salt concentrations, typically lower salt, in order to produce desired results, while amplification of smaller products may produce better results at higher salt concentrations. One of skill in the art will understand that the presence and/or concentration of a salt, along with alteration of salt concentrations, may alter the stringency of a biological or chemical reaction, and therefore any salt may be used that provides the appropriate conditions for a reaction of the present invention and as described herein.

Other components of a biological or chemical reaction may include a cell lysis component in order to break open or lyse a cell for analysis of the materials therein. A cell lysis component may include, but is not limited to, a detergent, a salt as described above, such as NaCl, KCl, ammonium sulfate [(NH4)2SO4], or others. Detergents that may be appropriate for the invention may include Triton X-100, sodium dodecyl sulfate (SDS), CHAPS (3-[(3-cholamidopropyl)dimethylammonio]-1-propanesulfonate), ethyl trimethyl ammonium bromide, nonyl phenoxypolyethoxylethanol (NP-40). Concentrations of detergents may depend on the particular application, and may be specific to the reaction in some cases. Amplification reactions may include dNTPs and nucleic acid primers used at any concentration appropriate for the invention, such as including, but not limited to, a concentration of 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM, 1 mM, 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, 100 mM, 150 mM, 200 mM, 250 mM, 300 mM, 350 mM, 400 mM, 450 mM, 500 mM, or the like. Likewise, a polymerase useful in accordance with the invention may be any specific or general polymerase known in the art and useful or the invention, including Taq polymerase, Q5 polymerase, or the like.

In some embodiments, amplification reagents as described herein may be appropriate for use in hot-start amplification. Hot start amplification may be beneficial in some embodiments to reduce or eliminate dimerization of adaptor molecules or oligos, or to otherwise prevent unwanted amplification products or artifacts and obtain optimum amplification of the desired product. Many components described herein for use in amplification may also be used in hot-start amplification. In some embodiments, reagents or components appropriate for use with hot-start amplification may be used in place of one or more of the composition components as appropriate. For example, a polymerase or other reagent may be used that exhibits a desired activity at a particular temperature or other reaction condition. In some embodiments, reagents may be used that are designed or optimized for use in hot-start amplification, for example, a polymerase may be activated after transposition or after reaching a particular temperature. Such polymerases may be antibody-based or aptamer-based. Polymerases as described herein are known in the art. Examples of such reagents may include, but are not limited to, hot-start polymerases, hot-start dNTPs, and photo-caged dNTPs. Such reagents are known and available in the art. One of skill in the art will be able to determine the optimum temperatures as appropriate for individual reagents.

Amplification of nucleic acids may be performed using specific thermal cycle machinery or equipment, and may be performed in single reactions or in bulk, such that any desired number of reactions may be performed simultaneously. In some embodiments, amplification may be performed using microfluidic or robotic devices, or may be performed using manual alteration in temperatures to achieve the desired amplification. In some embodiments, optimization may be performed to obtain the optimum reactions conditions for the particular application or materials. One of skill in the art will understand and be able to optimize reaction conditions to obtain sufficient amplification.

Also envisioned within the scope of the invention are methods for visualizing nucleic acids. In some embodiments, such methods may comprise, but are not necessarily limited to, direct fluorescence hybridization.

In some embodiments, the oligonucleotide may be single-stranded or double-stranded DNA, RNA, or a synthetic oligonucleotide. In specific embodiments, synthetic oligonucleotides may include, but are not necessarily limited to, peptide nucleic acids. In specific embodiments, the oligonucleotide comprises single-stranded RNA.

In some embodiments, the method may comprise quantifying expression of single-stranded RNA, mRNA and genomic RNA simultaneously. The target binding region may be sequence specific. The target oligonucleotide may comprise DNA, RNA, lincRNA, mRNA, viral RNAs, or a combination thereof. In some embodiments, each protein binding molecule bound to an oligonucleotide may be an oligonucleotide-tagged protein binding molecule that further comprises a poly-A sequence.

The method may further comprise admixing the population of cells with monomers of a polymerizable hydrogel and polymerizing the gel in an oil emulsion under conditions that allow covalent anchoring of nucleic acids and/or proteins to the hydrogel. Individual cells may be encapsulated in the individual discrete volume.

Emulsion may be achieved by a variety of methods known in the art (see, for example, US 2006/0078888 A1, of which paragraphs [0139]-[0143] are incorporated by reference herein). In some embodiments, the emulsion is stable to a denaturing temperature, for example, to 95° C. or higher. An exemplary emulsion is a water-in-oil emulsion. In some embodiments, the continuous phase of the emulsion includes a fluorinated oil. An emulsion can contain a surfactant or emulsifier (for example, a detergent, anionic surfactant, cationic surfactant, or amphoteric surfactant) to stabilize the emulsion. Other oil/surfactant mixtures, for example, silicone oils, may also be utilized in particular embodiments. An emulsion can be contained in a well or a plurality of wells, such as a plate, for easy of handling. In some examples, one or more target molecules, target nucleic acid and nucleic acid barcodes are compartmentalized. An emulsion can be a monodisperse emulsion or a polydisperse emulsion. Each droplet in the emulsion may contain, or contain on average, 0-1,000 or more target molecules. For instances, a given emulsion droplet may contain 0, 10, 20, 30, 40, 50, 100, 200, 300, 400, 500 or more target molecules. In particular embodiments, a given droplet may contain 0, 1, 2, or 3 cells capable of expressing or secreting target molecules, for example, a clonal population of target molecules. On average, the droplets of an emulsion of the present in disclosure may contain 0-3 cells capable of expressing or secreting target molecules, such as 0, 1, 2, or 3 cells capable of expressing or secreting target molecules, as rounded to the nearest whole number. In some embodiments, the number of cells capable of expressing or secreting target molecules in each emulsion droplet, on average, will be 1, between 0 and 1, or between 1 and 2. In other embodiments, the droplet may contain an acellular system, such as a cell-free extract.

The term "hydrogel" refers to any network of polymer chains that are hydrophilic, and sometimes found as a colloidal gel, in which water is the dispersion medium. Hydrogels are highly absorbent (they can contain over 90% water) natural or synthetic polymeric networks. Hydrogels also possess a degree of flexibility very similar to natural tissue, due to their significant water content. Hydrogel may include polyvinyl alcohol, sodium polyacrylate, acrylate polymers, copolymers with an abundance of hydrophilic groups, agarose, methylcellulose, hyaluronan, and other naturally derived polymers.

Hydrogels may be prepared by any means known in the art. Exemplary hydrogels may include acrylamide/bisacrylamide. The ratio of ratio of acrylamide to bisacrylamide may range from 10:1 to 40:1. In some embodiments, the percentage of acrylamide/bisacrylamide may range from 3% to 20%. In more specific embodiments, the percentage of acrylamide/bisacrylamide may range from 4% to 10%. In some embodiments, the hydrogel may include acrylamide/di-hydroxyethylenebisacrylamide. In some embodiments, the hydrogel may include acrylamide/N,N'-bis(acryloyl)cystamine. In some embodiments, cellular biomolecules may be covalently linked to the hydrogel.

In some embodiments, the hydrogel may further comprise primer pairs comprising releasable linkers, wherein the primers are barcoded using combinatorial indexing, and wherein said barcoded primers are incorporated into DNA or cDNA amplicons by the amplification step. Releasable linkers include, but are not necessarily limited to, cleavable linkers, such as photocleavable linkers, enzymatically cleavable linkers, chemically releasable linkers.

Hydrogelled single cells may be prepared by any means known in the art. As an exemplary protocol, an adaptation of a previously described protocol is listed below (doi: 10.103/nprot.2014.123):

| Make HM solution (400 mL) | | |
|---|---|---|
| 1. | Mix | For 4%/0.05% |
| | 40% wt/vol acrylamide | 40 ml |
| | 2% (wt/vol) bisacrylamide | 10 mL |
| | 10X PBS | 40 mL |
| | 16% (wt/vol) PFA | 100 mL |
| | Distilled water | 210 mL |
| | 0.1% (w/v) ammonium persulfate VA-044 thermal initiator | 1 g |
| 2. | Keep reagents on ice | |
| 3. | Make 10 ml aliquots and freeze at −20 C. | |
| Make SBC solution | | |
| 4. | Prepare stock of 20% (wt/vol) DS in H20 (store at RT for weeks) | For 4%/0.05% |
| | 40% wt/vol acrylamide | 40 ml |
| 5. | Prepare 1M boric acid buffer (pH adjusted to 8.5). 10 g boric acid, 61.83 g NaOH. Dissolve in 700-800 mL, pH 8.5, and Q.S. to 1 L. With a little heat is | |
| 6. | Freshly prepare clearing buffer by diluting 4&5 five-fold in distilled water and combine them | |

Procedure

7. Prepare the HM stock solution by thawing frozen vials on ice or in a refrigerator. Gently mix the thawed monomer solution by inverting. Keep all reagents on ice during the whole procedure. CRITICAL STEP Make sure that there is no precipitation floating in the monomer solution; this is an indicator of spontaneous polymerization of the stored monomer solution.

8. Incubate the cell in HM (0.5-1 k cells/L).

9. Put samples in coolrack, open cap, and leave in dessicator vacuum for 10 minutes.

10. Disconnect vacuum, keep nitrogen just above atmospheric pressure run microfluidic droplet formation whereby microfluidic channel size is adapted to generate droplets slightly larger than the cell size.

11. Use Biorad oil for droplet generation spiked with 0.4% TMED.

12. Incubate at 60 C in thermocycler overnight.

13. Wash sample twice with SBC buffer for 1 h at room temperature to dialyzed the remaining PFA, initiator and monomer.

14. Passive clearing of hydrogel-embedded tissue by gentle shaking in SBC buffer at 37/60° C. for 2-6 hours.

15. Wash with boric acid buffer (0.2M/pH 8.5 with 0.1% (vol/vol) Triton X-100) for 1-3 h at 37° C.

16. Resuspend cells in PBST (0.1% Triton X in 1×PBS) for 30 min.

17. Incubate in antibody/PST solution for 2-6 hours at 37° C., DAP (1 ug/ml), can also be added at this step.
18. Wash off the antibodies with PBST at 4° C. for 2 hours.
19. Samples can be stored in PBST (with 0.01% (wt/vol) sodium azide) at 4° C. for up to a week.

The method may further comprise barcoding target nucleic acids using unique nucleic acid identifiers, for example origin-specific barcodes and the like. The nucleic acid identifiers, nucleic acid barcodes, can include a short sequence of nucleotides that can be used as an identifier for an associated molecule, location, or condition. In certain embodiments, the nucleic acid identifier further includes one or more unique molecular identifiers and/or barcode receiving adapters. A nucleic acid identifier can have a length of about, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 base pairs (bp) or nucleotides (nt). In certain embodiments, a nucleic acid identifier can be constructed in combinatorial fashion by combining randomly selected indices (for example, about 1, 2, 3, 4, 5, 6, 7, 8, 9, or 10 indexes). Each such index is a short sequence of nucleotides (for example, DNA, RNA, or a combination thereof) having a distinct sequence. An index can have a length of about, for example, 4, 5, 6, 7, 8, 9, 10, 11, 12, 13, 14, 15, 16, 17, 18, 19, 20, 21, 22, 23, 24, or 25 bp or nt. Nucleic acid identifiers can be generated, for example, by split-pool synthesis methods, such as those described, for example, in International Patent Publication Nos. WO 2014/047556 and WO 2014/143158, each of which is incorporated by reference herein in its entirety, or by split-pool ligation methods as described in Quinodoz et al. (Biorxiv "Higher-order inter-chromosomal hubs shape 3-dimensional genome organization in the nucleus" (2017)).

In certain example embodiments, the method further comprises introducing amplification reagents to the hydrogel droplet. Labeled target molecules and/or target nucleic acids associated origin-specific nucleic acid barcodes (optionally in combination with other nucleic acid barcodes as described herein) can be amplified by methods known in the art, such as polymerase chain reaction (PCR). For example, the nucleic acid barcode can contain universal primer recognition sequences (or universal primer binding sequences (UBS)) that can be bound by a PCR primer for PCR amplification and subsequent high-throughput sequencing. In certain embodiments, the nucleic acid barcode includes or is linked to sequencing adapters (for example, universal primer recognition sequences) such that the barcode and sequencing adapter elements are both coupled to the target molecule. In particular examples, the sequence of the origin specific barcode is amplified, for example using PCR. In some embodiments, an origin-specific barcode further comprises a sequencing adaptor. In some embodiments, an origin-specific barcode further comprises universal priming sites (UPS). A nucleic acid barcode (or a concatemer thereof), a target nucleic acid molecule (for example, a DNA or RNA molecule), a nucleic acid encoding a target peptide or polypeptide, and/or a nucleic acid encoding a specific binding agent may be optionally sequenced by any method known in the art, for example, methods of high-throughput sequencing, also known as next generation sequencing or deep sequencing. A nucleic acid target molecule labeled with a barcode (for example, an origin-specific barcode) can be sequenced with the barcode to produce a single read and/or contig containing the sequence, or portions thereof, of both the target molecule and the barcode. Exemplary next generation sequencing technologies include, for example, Illumina sequencing, Ion Torrent sequencing, 454 sequencing, SOLiD sequencing, and nanopore sequencing amongst others. In some embodiments, the sequence of labeled target molecules is determined by non-sequencing based methods. For example, variable length probes or primers can be used to distinguish barcodes (for example, origin-specific barcodes) labeling distinct target molecules by, for example, the length of the barcodes, the length of target nucleic acids, or the length of nucleic acids encoding target polypeptides. In other instances, barcodes can include sequences identifying, for example, the type of molecule for a particular target molecule (for example, polypeptide, nucleic acid, small molecule, or lipid). For example, in a pool of labeled target molecules containing multiple types of target molecules, polypeptide target molecules can receive one identifying sequence, while target nucleic acid molecules can receive a different identifying sequence. Such identifying sequences can be used to selectively amplify barcodes labeling particular types of target molecules, for example, by using PCR primers specific to identifying sequences specific to particular types of target molecules. For example, barcodes labeling polypeptide target molecules can be selectively amplified from a pool, thereby retrieving only the barcodes from the polypeptide subset of the target molecule pool.

In certain other example embodiments, a recombinase polymerase amplification (RPA) reaction may be used to amplify the target nucleic acids. RPA reactions employ recombinases which are capable of pairing sequence-specific primers with homologous sequence in duplex DNA. If target DNA is present, DNA amplification is initiated and no other sample manipulation such as thermal cycling or chemical melting is required. The entire RPA amplification system is stable as a dried formulation and can be transported safely without refrigeration. RPA reactions may also be carried out at isothermal temperatures with an optimum reaction temperature of 37-42° C. The sequence specific primers are designed to amplify a sequence comprising the target nucleic acid sequence to be detected. In certain example embodiments, a RNA polymerase promoter, such as a T7 promoter, is added to one of the primers. This results in an amplified double-stranded DNA product comprising the target sequence and a RNA polymerase promoter. After, or during, the RPA reaction, a RNA polymerase is added that will produce RNA from the double-stranded DNA templates. The amplified target RNA can then in turn be detected by the CRISPR effector system. In this way target DNA can be detected using the embodiments disclosed herein. RPA reactions can also be used to amplify target RNA. The target RNA is first converted to cDNA using a reverse transcriptase, followed by second strand DNA synthesis, at which point the RPA reaction proceeds as outlined above.

In some embodiments, macromolecules are covalently fixed to the hydrogel using LabelX (for nucleic acids) or AcX (for proteins). Methods for making LabelX and/or AcX are known in the art and may be found in Chen et al. (Science 347(6221):543-548; 2015), Chen et al. (Nat Methods 13:679-684; 2016), and Tillberg et al. (Nat Biotechnol 34:987-992; 2016). In some embodiments, cell fixation is reversed using proteinase K treatment, heat treatment, and/or other methods specific to the fixation protocol.

The method may further comprise breaking the emulsions to release the individual discrete volume and adding oligonucleotide-tagged protein binding molecules. The oligonucleotide-tagged protein binding molecules may be added either before or after hydrogel polymerization. PCR may be performed in the individual discrete volumes, thereby generating cell-barcoded amplicons. The resulting amplicons may then be sequenced, as described elsewhere herein.

In specific embodiments, the cells may be fixed before preparing the hydrogel droplets. Any standard fixation methods known in the art may be used. Fixation of cells or tissue may involve but is not necessarily limited to, the use of cross-linking agents, such as formaldehyde, and may involve embedding cells or tissue in a paraffin wax or polyacrylamide support matrix (Chung K, et al. Nature. 2013 May 16; 497(7449): 322-7). Standard methods for delivery of nucleic acid based probes to fixed cells may be used. Example methods for delivering to fixed cells may be found in U.S. Patent Application Publication No. 2017/0067096 A1, International Patent Application No. PCT/US2015/016788, and U.S. Patent Application no. 2016/0305856 A1, each of which is incorporated herein by reference.

In some embodiments, the method may allow for measuring of both intracellular and extracellular proteins.

Methods for Measuring Protein Abundance in Single Cells

Further embodiments of the invention may comprise methods for measuring proteins in single cells. Such methods may involve delivering a mixture of any of the compositions described herein to a population of cells. As such, individual cells may be encapsulated in an individual discrete volume as described herein. The individual discrete volume may comprise PCR primers on a bead as described herein. The oligonucleotide of the composition may then be amplified using PCR and the target protein abundance may be quantified and/or the target protein localization may be determined based at least in part on sequencing of amplicons.

In specific embodiments, the target binding region may be sequence specific.

In some embodiments, the protein binding molecule may be an antibody as described herein. As described herein, detection of the nucleotide sequence of the origin specific barcode handle sequence may comprise nucleic acid sequencing, amplification, hybridization, or any combination thereof.

As described herein, in certain embodiments the individual discrete volume may be a hydrogel droplet.

Also envisioned within the scope of these methods are methods for visualizing nucleic acids. Any method known in the art for visualizing nucleic acids may be used. Such methods include, but are not necessarily limited to, electrophoresis, PCR, qPCR, sequencing, southern blotting, northern blotting, direct fluorescence hybridization, fluorescence in situ hybridization, or in situ sequencing. In specific embodiments, nucleic acids may be visualized by direct fluorescence hybridization.

As described herein, the oligonucleotide may be single-stranded or double-stranded DNA, RNA, or a synthetic oligonucleotide. In specific embodiments, the synthetic oligonucleotide may be a peptide nucleic acid.

In some embodiments, the method may further comprise measurement of target oligonucleotides in addition to protein. Such target oligonucleotides may include, but are not necessarily limited to, DNA, RNA, lincRNA, mRNA, viral RNAs, or a combination thereof.

In some embodiments, each protein binding molecule bound to an oligonucleotide may be an oligonucleotide-tagged protein binding molecule that further comprises a poly-A sequence.

In some embodiments, the method may further comprise delivering one or more ligation dependent probes to the cells. A ligation dependent probe (or proximity probe) is a probe that comprises a target binding region configured to bind a target polynucleotide and a primer binding site region. Ligation dependent probes may be used in a set of two or more. Ligation dependent probes may comprise a set of individual ligation dependent probes, with each individual ligation dependent probe configured to hybridize to a specific target nucleic acid sequence on a target polynucleotide. Target sequences on the target polynucleotide are selected to be close enough in distance on the target polynucleotide such that ligation dependent probes hybridized to said target nucleic acid sequences may be subsequently ligated together. Accordingly, in certain embodiments, ligation dependent probe pairs may bind within 1 nucleotides of on another. In some embodiments, the ligation dependent probe pairs may bind within 2 to 500 nucleotides of one another, the gap between which is filled through polymerase extension, or another polynucleotide filler, prior to ligation. Alternatively, a ligation dependent probe may be a single molecule comprising two or more target binding regions connected by linker sequences. The target binding regions comprise a nucleic acid sequence selected to hybridize to a target region on a target polynucleotide. Linker sequences are selected such that the molecule may adapt a conformation that allows the individual target binding regions to hybridize to adjacent regions on the target polynucleotide. Target sequences on the target polynucleotide are selected to be close enough in distance on the target polynucleotide such that ligation dependent probes hybridized to said target nucleic acid sequences may be subsequently ligated together. Accordingly, in certain embodiments, ligation dependent probe pairs may bind within 1, 2, 3, 4, or 5 nucleotides of one another. In certain example embodiments, the ligation dependent probes comprising two or more target binding regions may be based on molecule inversion probes (MIP), or "padlock probes." See e.g. Niedzicka et al. Sci Rep. 2016; 6:24501.

In the case of MIPs, padlock probes, and rolling circle probes, constructs for generating labeled target sequences are formed by circularizing a linear version of the probe in a template-driven reaction on a target polynucleotide followed by digestion of non-circularized polynucleotides in the reaction mixture, such as target polynucleotides, unligated probe, probe concatemers, and the like, with an exonuclease, such as exonuclease I.

Ligation dependent probes may be RNA, DNA, or a combination thereof. Ligation dependent probes may vary in length from 10 to 200 nucleotides. To allow for amplification, the ligation dependent probes may further comprise a primer binding site. The same or different primer binding site may be found on each ligation dependent probe. In certain embodiments, a set of ligation dependent probes, each ligation dependent probe comprising target binding region to a different target nucleic acid sequence on the same or different target polynucleotide, but the same primer binding set on each ligation dependent probe.

In one embodiment, the ligation dependent probes are designed to bind one or more target RNA molecules in a cell. The ligation dependent probes may be configured to bind to select RNA fragments or RNA exons for the purpose of quantifying the amount of the selected RNA fragment or exon in a sample, or configured to hybridize to a specific RNA sequence variant to detect and identify the presence of said variant in a sample.

Ligation dependent probes are delivered to a sample containing the target molecules of interest. The method of delivery will depend on the sample type. Samples sources may include biological samples of a subject, or environmental samples. These samples may be solids or liquids. The biological samples may include, but are not limited to, animal tissues such as those obtained by biopsy or post mortem, including saliva, blood, semen, plasma, sera, stool, urine, sputum, mucous, lymph, synovial fluid, spinal fluid, cerebrospinal fluid, a swab from skin or a mucosal membrane, or combination thereof. Other biological samples may include plant tissues such as leaves, roots, stems, fruit, and seeds, or sap or other liquids obtained when plant tissues are cut or plant cells are lysed or crushed. Environmental samples may include surfaces or fluids. In an example embodiment, the environmental sample is taken from a solid surface, such as a surface used in the preparation of food or other sensitive compositions and materials.

In specific embodiments, ligation dependent probes may comprise sequences that bind in proximate locations on a target RNA, as well as a first primer handle sequence, a second primer handle sequence, or both. The bound ligation dependent probes may then be linked. The oligonucleotide of the composition and the linked ligation dependent probes may be amplified using barcoded PCR primers. The barcode may be incorporated into each resulting amplicon and the target protein abundance may be quantified and/or target protein localization may be determined based at least in part on sequencing of amplicons as described herein.

Methods for linking the one or more ligation dependent probes include any methods known in the art such as, but not necessarily limited to, ligation, splinted ligation, hybridization, or proximity extension.

In specific embodiments, the one or more ligation dependent probes may be molecular inversion probes (MIPs), padlock probes, or split-ligation probes.

In specific embodiments, each probe may further comprise a unique molecular identifier (UMI) as described herein. As described herein, a nucleic acid barcode or UMI can have a length of at least, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 nucleotides, and can be in single- or double-stranded form.

Methods may further comprise admixing the population of cells with monomers of a polymerizable hydrogel and polymerizing the gel in an oil emulsion under conditions that allow covalent anchoring of nucleic acids and/or proteins to the hydrogel. As such, individual cells may be encapsulated in the individual discrete volume. The emulsions may then be broken to release the individual discrete volume. Oligonucleotide-tagged protein binding molecules may be added either before or after hydrogel polymerization. PCR may then be performed in the individual discrete volumes, generating cell-barcoded amplicons. The resulting amplicons may then be sequenced. In certain embodiments, the cells may be fixed before preparing the hydrogel droplets. In specific embodiments, the method may allow for measuring of both intracellular and extracellular proteins.

Methods for Measuring Protein Abundance and Localization in Situ

Also envisioned within the scope of the invention are methods for determining the quantity and location of proteins within single cells. Such methods may comprise encapsulating cells or tissue in a hydrogel as described herein. The cells or tissue may be treated with any of the compositions described herein. The method may further comprise delivering one or more ligation dependent probes to the cells as described herein. The ligation dependent probes may comprise a sequence that is complementary to the first primer handle sequence and a sequence that is complementary to the second primer handle sequence as described herein. The oligonucleotide of the composition may then be amplified using the ligation dependent probes, allowing the amplified oligonucleotide to be incorporated into each resulting amplicon. Target protein abundance may then be quantified and/or target protein localization may be determined at least in part on sequencing of amplicons as described herein.

In specific embodiments, the protein binding molecule may be an antibody as described herein. In specific embodiments, the cells may be fixed before delivering the ligation dependent probes. In specific embodiments, the amplification reagents may be rolling circle amplification reagents. As described herein, the ligation dependent probes may be molecular inversion probes (MIPs), padlock probes, or split-ligation probes.

The method may further comprise delivering one or more additional ligation dependent probes to the cells for measuring target mRNA.

In specific embodiments, the individual discrete volumes may be hydrogel droplets as described herein. Methods for visualizing proteins are envisioned within the scope of this particular method. Such methods may include, but are not necessarily limited to, immunohistochemistry, or in situ imaging.

Also envisioned are reporter sequences that enable cellular recording, as described elsewhere herein. As described herein, amplicons may be sequenced using a fluorescence in situ sequencing method.

Methods for Quantifying and Identifying Protein in Individual Molecule Complexes Also envisioned within the scope of the invention are methods for quantifying protein in individual molecule complexes. Such methods may comprise fixing a population of cells such that oligonucleotide-protein complexes are formed. The method may further comprise delivering a mixture of any of the compositions described herein to the oligonucleotide-protein complexes. The complexes may then be encapsulated in an individual discrete volume, wherein the individual discrete volume comprises PCR primers on a bead as described herein. The PCR primers may be barcoded PCR primers. The individual discrete volume may then be suspended in a reverse transcription mixture and the nucleotide sequence of the origin specific barcode may be detected, thereby assigning the target oligonucleotide and protein of interest to a specific individual discrete volume while maintaining information about sample origin of the target oligonucleotide. The individual discrete volume may be a hydrogel droplet.

As described elsewhere herein, the protein binding molecule may be an antibody. Detection of the nucleotide sequence of the origin specific barcode handle sequence may comprise nucleic acid sequencing, amplification, hybridization, or any combination thereof as described elsewhere herein. The oligonucleotide may be single-stranded or double-stranded DNA, RNA, or a synthetic oligonucleotide. The oligonucleotide may comprise single-stranded RNA. The synthetic oligonucleotide may be a peptide nucleic acid.

Also within the scope of the invention are methods for visualizing nucleic acids, such as, but not necessarily limited to, direct fluorescence hybridization.

In some embodiments, the method comprises quantifying expression of single-stranded RNA, mRNA and genomic RNA simultaneously.

In some embodiments, the target binding region may be sequence specific. The target oligonucleotide may comprise DNA, RNA, lincRNA, mRNA, viral RNAs, or a combination thereof. In some embodiments, each protein binding molecule bound to an oligonucleotide may be an oligonucleotide-tagged protein binding molecule that further comprises a poly-A sequence.

The method may further comprise admixing the oligonucleotide-protein complexes with monomers of a polymerizable hydrogel and polymerizing the gel in an oil emulsion under conditions that allow covalent anchoring of nucleic acids and/or proteins to the hydrogel as described elsewhere herein. The individual complexes may thus be encapsulated in the individual discrete volume and the emulsions may be broken to release the individual discrete volume. Oligonucleotide-tagged protein binding molecules may then be added either before or after hydrogel polymerization. PCR may be performed in the individual discrete volumes, generating cell-barcoded amplicon, and the resulting amplicons may be sequenced, as described elsewhere herein.

In some embodiments, the complexes may be fixed before preparing the hydrogel droplets. In some embodiments, the method may allow for measuring of both intracellular and extracellular proteins as described herein.

In other embodiments, methods for quantifying protein in individual molecule complexes may comprise fixing a population of cells, lysing the cells, and encapsulating the resulting individual molecule complexes with any of the compositions described herein in an individual discrete volume. The individual discrete volume may comprise PCR primers on a bead. The oligonucleotide of the composition may then be amplified using PCR, and target protein abundance may be quantified and/or target protein localization may be determined based at least in part on sequencing of amplicons.

As described herein, the protein binding molecule may be an antibody. Detection of the nucleotide sequence of the origin specific barcode handle sequence may comprise nucleic acid sequencing, amplification, hybridization, or any combination thereof. The individual discrete volume may be a hydrogel droplet.

Also within the scope of this method are methods for visualizing nucleic acids, such as, but not necessarily limited to direct fluorescence hybridization.

In some embodiments, the oligonucleotide may be single-stranded or double-stranded DNA, RNA, or a synthetic oligonucleotide. The synthetic oligonucleotide may be a peptide nucleic acid as described herein. The target binding region may be sequence specific.

The method may further comprise measurement of target oligonucleotides in addition to protein. As such, the target oligonucleotides may comprise DNA, RNA, lincRNA, mRNA, viral RNAs, or a combination thereof.

Each protein binding molecule bound to an oligonucleotide may be an oligonucleotide-tagged protein binding molecule that further comprises a poly-A sequence.

The method may further comprise delivering one or more ligation dependent probes to the oligonucleotide-protein complexes. The ligation dependent probe may comprise sequences that bind in proximate locations on a target RNA and the first primer handle sequence, the second primer handle sequence, or both. The bound ligation dependent probes may then be linked, and the oligonucleotide of the composition and the linked ligation dependent probes may then be amplified using barcoded PCR primers. The barcode may be incorporated into each resulting amplicon, and target protein abundance may be quantified and/or target protein localization may be determined based at least in part on sequencing of amplicons.

The method may further comprise admixing the oligonucleotide-protein complexes with monomers of a polymerizable hydrogel and polymerizing the gel in an oil emulsion under conditions that allow covalent anchoring of nucleic acids and/or proteins to the hydrogel. Individual complexes may thus be encapsulated in the individual discrete volume. The emulsions may be broken to release the individual discrete volume, and oligonucleotide-tagged protein binding molecules may be added either before or after hydrogel polymerization. PCR may be performed in the individual discrete volumes, thus generating cell-barcoded amplicons, then allowing for sequencing the resulting amplicons.

In some embodiments, the cells may be fixed before preparing the hydrogel droplets. In some embodiments, the method may allow for measuring of both intracellular and extracellular proteins.

Systems and Kits

In another aspect, the invention described herein provides a molecular assay system comprising a set of oligonucleotide-tagged protein binding molecules, amplification reagents, and droplet forming reagents for formation of hydrogel-based droplets, as described herein.

In some embodiments, the oligonucleotide-tagged protein binding molecules may comprise an origin specific barcode handle sequence, a first primer handle sequence, a second primer handle sequence, and a target binding region.

The oligonucleotide-tagged protein binding molecules may further comprise an adapter sequence. The oligonucleotide-tagged protein binding molecules may further comprise a UMI. In some embodiments, the protein binding molecules may be antibodies, aptamers, peptides, avimers, small molecules, recombinant proteins, protein-binding derivatives, or nucleic acid molecules. In specific embodiments, the protein binding molecules may be antibodies. In specific embodiments, the first primer handle sequence may comprise CACCCGAGAATTCCA (SEQ ID NO: 1) and the second primer handle sequence may comprise CTCGATAGCC (SEQ ID NO:2).

In some embodiments, the oligonucleotides may comprise single-stranded RNA. In other embodiments, the oligonucleotides may comprise single-stranded or double-stranded DNA or synthetic oligonucleotides. The oligonucleotides may further comprise a poly-A sequence.

In some embodiments, the system may further comprise a set of ligation dependent probes, such as, but not necessarily limited to, molecular inversion probes (MIPs), padlock probes, or split-ligation probes.

The amplification reagents comprised in the system may include, but are not necessarily limited to, whole genome amplification regents, PCR amplification reagent, reverse transcription reagents, rolling circle amplification reagents, or a combination thereof.

Also envisioned within the scope of the invention are kits comprising a panel of oligonucleotides, a panel of protein binding molecules, and optionally, reagents for coupling the protein binding molecules to the oligonucleotides. Each oligonucleotide may comprise an origin specific barcode handle sequence, a first primer handle sequence, a second primer handle sequence, and a target binding region.

In some embodiments, the oligonucleotides and the protein binding molecules may be coupled together using any of the methods described herein.

The protein binding molecules may include, but are not necessarily limited to, antibodies, aptamers, peptides, avimers, small molecules, recombinant proteins, protein-binding derivatives, or nucleic acid molecules. In specific embodiments, the protein binding molecules may be antibodies.

In some embodiments, the antibodies may target receptors on immune cells. In other embodiments, the antibodies may target specific markers in intracellular signaling pathways. In yet other embodiments, the antibodies may target transcription factors.

The invention is further described in the following examples, which do not limit the scope of the invention described in the claims.

Connecting Protein Binding Molecules to Oligonucleotide Tags

Various methods have been developed to conjugate oligonucleotides to protein-binding molecules. The conjugation may be a chemical conjugation (e.g., via a linker) or a physical conjugation (e.g., without necessarily requiring a linker), such that the oligonucleotide can be removed from the protein-binding molecule via cleavage. Heterobifunctional cross-linkers, such as succinimidyl 4-hydrazinonicotinate acetone hydrazone (SANH) (Mocanu et al. Proteomics 11(10):2063-2070; 2011) and succinimidyl 4-(N-maleimidomethyl) cyclohexane-1-carboxylate (SMCC) (Soderberg et al. Nature Methods 3(12):995-1000; 2006), are often used to introduce a bridge between an oligonucleotide and an antibody, for example. Commercial kits are also available for the production of oligonucleotide-conjugated antibodies. Examples include the Solulink Antibody-Oligonucleotide All-in-One Conjugation Kit, and the Innova Thunder-Link kit. However, these methods may be labor intensive and costly, and are not suitable for large-scale production of oligonucleotide-conjugated antibodies needed for multiplex protein detection.

The copper-catalyzed alkyne-azide cycloaddition (CuAAC), or click reaction, has been used to modify biomolecules in various applications (Zeng et al. J. Nucl. Med. 54:829-832; 2013). Although robust, CuAAC is not suitable for applications involving functional biomolecules because copper ions may be detrimental to these molecules. For example, copper ions can cause protein denaturation (Manova et al. Langmuir 28(23):8651-8663; 2012). To circumvent this issue, a Cu-free click reaction based on strain-promoted alkyne-azide cycloaddition (SPAAC) has been developed (Manova et al. Langmuir 28(23):8651-8663; 2012, van Hest et al. ChemBioChem 12(9):1309-1312; 2011). In SPAAC, cyclooctynes such as difluorinated cyclooctyne (DIFO) and dibenzocyclooctyne (DBCO) are used to react with azide-functionalized molecules. The reaction is performed under physiological conditions and has no adverse effects on macro-biomolecules such as antibodies.

In certain embodiments, a streptavidin-biotin interaction may be used to link oligonucleotides to antibodies or other protein binding molecules. In certain embodiments, the antibody-oligonucleotide includes a disulfide link at the 5' end of the oligonucleotide which allows the oligo to be released from the antibody with reducing agents. In certain embodiments, highly specific, FACS optimized monoclonal or polyclonal antibodies are selected.

Antibodies may be conjugated to oligonucleotides containing sample barcode sequences and a polyA tail. Oligonucleotides may be conjugated to antibodies by streptavidin-biotin conjugation using the LYNX Rapid Streptavidin Antibody Conjugation Kit (Bio-Rad, USA), according to manufacturer's instructions with modifications. Specifically, Applicants can label 15 µg of antibody with 10 µg of streptavidin. At this ratio, up to two streptavidin tetramers can theoretically be conjugated to one antibody, which results in 4-8 binding sites for biotin on each antibody. DNA-oligonucleotides can be purchased and/or synthesized with a 5' biotin modification or with a 5' amine modification and biotinylated using NHS-chemistry according to manufacturer's instructions (EZ Biotin S-S NHS, Thermo Fisher Scientific, USA). The disulfide bond allows separation of the oligo from the antibody with reducing agents. Separation of the oligo from the antibody may not be needed for all applications. Excess Biotin-NHS can be removed by gel filtration (Micro Biospin 6, Bio-Rad) and ethanol precipitation. Streptavidin-labelled antibodies can be incubated with biotinylated oligonucleotides in excess (1.5× theoretically available free streptavidin) overnight at 4° C. in PBS containing 0.5M NaCl and 0.02% Tween. Unbound oligo can be removed from antibodies using centrifugal filters with a 100 KDa MW cutoff (Millipore, USA). Removal of excess oligo can be verified by 4% agarose gel electrophoresis. Antibody-oligo conjugates can be stored at 4° C. supplemented with sodium azide and BSA.

In some embodiments, an oligonucleotide may be attached to a protein-binding through the sequential addition of a dibenzocyclooctyne (DBCO) moiety and an azide-modified oligonucleotide. The reaction condition and purification process may be optimized to achieve maximum yield and best performance in the functional test using an oligonucleotide extension reaction. In the extension assay a pair of antibody binders (two antibodies, each conjugated with its own oligonucleotide) is developed for each protein target. The two oligonucleotides contain a six-base complementary region at their 3' prime ends to allow annealing and extension by DNA synthesis enzymes to form a DNA template. The template is then detected by qPCR. Distinct oligonucleotide sequences are assigned to different antibody binders to enable multiplex protein detection. The assays may be tested using recombinant proteins and cell lysates, and in single cells using the Fuidigm C1 system. The strain-promoted alkyne-azide cycloaddition (SPAAC)-based conjugation method is simple and cost-effective and is well-suited for the preparation of oligonucleotide-conjugated antibodies for multiplex protein assays.

In other embodiments, antibodies may be chemically cross-linked to a substrate that contains free amino or carboxyl groups using glutaraldehyde or carbodiimides as cross-linker agents. In this method, aqueous solutions containing free antibodies are incubated with the solid-state substrate in the presence of glutaraldehyde or carbodiimide. For crosslinking with glutaraldehyde the reactants can be incubated with 2% glutaraldehyde by volume in a buffered solution such as 0.1 M sodium cacodylate at pH 7.4. Other standard immobilization chemistries are known by those of skill in the art.

EXAMPLES

Example 1—CITE-Seq with Genomics Platform

Oligonucleotides and protein may be measured simultaneously in single cells using the following method. Cells may be harvested and mixed with a mixture of DNA-tagged antibodies according to FIG. 1. The cells may then be encapsulated in hydrogel droplets. The hydrogel droplets may be suspended in a reverse transcription mixture and the nucleotide sequence of the origin specific barcode may be determined. This allows one to assign the target oligonucleotide and protein of interest to a specific hydrogel droplet, while maintaining information about sample origin of the target oligonucleotide (see Stoeckius et al. Nat Methods 14(9):865-868; 2017).

Example 2—Single-Cell Protein Measurements

Protein abundance may be measured in single cells using the following method. Single cells may be stained with a mixture of DNA-tagged antibodies according to FIG. 1. Optionally, cells may be fixed to allow for analysis of both intracellular and extracellular proteins. Cells may then be encapsulated into hydrogel droplets harboring PCR primers on a bead. The DNA of the DNA-tagged antibodies may then be amplified by PCR and amplicons may be sequenced. Sequences provide information about target protein abundance and target protein localization.

Example 3—In Situ Measurements of Protein Abundance and Localization

The quantity and location of proteins within single cells can be determined by the following method. Cells or tissue may be encapsulated in a hydrogel droplet and mixed with a mixture of DNA-tagged antibodies according to FIG. 1. Optionally, cells may be fixed at this point. The cells are then mixed with a mixture of padlock probes that hybridize to the PCR handles on the DNA-tagged antibodies. The padlock probes may then be used to amplify the construct using a method such as rolling circle amplification, for example. The resulting amplicons may be sequenced using Illumina technology, or other suitable methods. This ultimately provides information about quantity and localization of target proteins.

Example 4—Single-Complex Protein Measurements and Identification

Protein may be quantified in individual molecule complexes using the following Method. Harvested Cells May be Crosslinked Such that Oligonucleotide-Protein Complexes are formed, and these complexes may then be mixed with a mixture of DNA-tagged antibodies according to FIG. 1. The complexes may be encapsulated in individual droplets harboring PCR primers on a bead. The droplets may then be suspended in a mixture containing reverse transcription reagents and the nucleotide sequence of the origin specific barcode may be determined. This allows one to assign the target oligonucleotide and protein of interest to a specific hydrogel droplet, while maintaining information about sample origin of the target oligonucleotide. Optionally, this method allows for multiplexing with other types of measurements, such as quantification of RNA and DNA, for example.

Example 5—Single-Complex Protein Measurements and Identification

Proteins may be quantified in individual molecule complexes using the following method. Harvested cells may be crosslinked, fragmented, and the resulting individual molecule complexes may be encapsulated in a hydrogel droplet with a DNA-tagged antibody according to FIG. 1. The DNA may then be amplified using primers present in the hydrogel droplet, and resulting amplicons may be sequenced, allowing for quantification of protein abundance and/or determination of target protein localization. Optionally, an adapter may be ligated onto the 3' end of the DNA-tagged antibody, allowing for split-pool ligation methods (see Quinodoz et al. bioRxiv November, 2017).

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A construct comprising a protein binding molecule bound to an oligonucleotide tag, wherein the oligonucleotide tag comprises an origin specific barcode sequence, a first primer handle sequence, a second primer handle sequence, and a target binding region, wherein the first primer handle sequence, the second primer handle sequence or both are capable of binding a padlock probe.

2. The construct of claim 1, further comprising an adapter sequence.

3. The construct according to claim 1, wherein the oligonucleotide tag further comprises a unique molecular identifier (UMI).

4. The construct according to claim 1, wherein the protein binding molecule is an antibody, aptamer, peptide, avimer, small molecule, recombinant protein, protein-binding derivative, or nucleic acid molecule.

5. The construct of claim 4, wherein the protein binding molecule is an antibody.

6. The construct of claim 1, wherein the oligonucleotide tag comprises single stranded RNA.

7. The construct of claim 1, wherein the oligonucleotide tag comprises single-stranded or double-stranded DNA or a synthetic oligonucleotide.

8. The construct of claim 1, wherein the oligonucleotide tag further comprises a poly-A sequence.

9. The construct of claim 1, wherein the first primer handle sequence comprises SEQ ID NO:1 and the second primer handle sequence comprises SEQ ID NO:2.

10. A method for simultaneously measuring target oligonucleotides and protein in single cells comprising:
   delivering the construct of claim 1 to a population of cells;
   encapsulating individual cells in an individual discrete volume, wherein the individual discrete volume comprises PCR primers on a bead;
   suspending the individual discrete volume in a reverse transcription mixture; and
   detecting the nucleotide sequence of the origin specific barcode sequence, thereby assigning the target oligonucleotide and protein of interest to a specific individual discrete volume, while maintaining information about sample origin of the target oligonucleotide.

11. The method of claim 10, wherein the protein binding molecule is an antibody.

12. The method of claim 10, wherein detecting the nucleotide sequence of the origin specific barcode sequence comprises nucleic acid sequencing, amplification, hybridization, or any combination thereof.

13. The method of claim 10, wherein the individual discrete volume is a hydrogel droplet.

14. The method of claim 10, further comprising methods for visualizing nucleic acids.

15. The method of claim 14, wherein the methods for visualizing nucleic acids comprise direct fluorescence hybridization.

16. The method of claim 10, wherein the oligonucleotide is single-stranded or double-stranded DNA, RNA, or a synthetic oligonucleotide.

17. The method of claim 10, wherein the oligonucleotide comprises single-stranded RNA.

18. The method of claim 17, wherein the method comprises quantifying expression of single-stranded RNA, mRNA and genomic DNA simultaneously.

19. The method of claim 16, wherein the synthetic oligonucleotide is a peptide nucleic acid.

20. The method of claim 10, wherein the target binding region is sequence specific.

21. The method of claim 10, wherein the target oligonucleotide comprises DNA, RNA, lincRNA, mRNA, viral RNAs, or a combination thereof.

22. The method of claim 10, wherein each protein binding molecule bound to an oligonucleotide is an oligonucleotide-tagged protein binding molecule that further comprises a poly-A sequence.

23. The method of claim 10, further comprising admixing the population of cells with monomers of a polymerizable hydrogel and polymerizing the gel in an oil emulsion under conditions that allow covalent anchoring of nucleic acids and/or proteins to the hydrogel, wherein individual cells are encapsulated in the individual discrete volume;
breaking the emulsions to release the individual discrete volume;
adding oligonucleotide-tagged protein binding molecules, either before or after hydrogel polymerization;
performing PCR in the individual discrete volumes, wherein cell-barcoded amplicons are generated; and
sequencing the resulting amplicons.

24. The method of claim 10, wherein the cells are fixed before preparing the hydrogel droplets.

25. The method of claim 21, wherein the method allows for measuring of both intracellular and extracellular proteins.

26. A method for measuring proteins in single cells comprising:
delivering of the construct of claim 1 to a population of cells;
encapsulating individual cells in an individual discrete volume, wherein the individual discrete volume comprises PCR primers on a bead;
amplifying the oligonucleotide of the construct using PCR; and
quantifying target protein abundance and/or determining target protein localization based at least in part on sequencing of amplicons.

27. The method of claim 26, wherein the protein binding molecule is an antibody.

28. The method of claim 26, wherein detecting the nucleotide sequence of the origin specific barcode sequence comprises nucleic acid sequencing, amplification, hybridization, or any combination thereof.

29. The method of claim 26, wherein the individual discrete volume is a hydrogel droplet.

30. The method of claim 26, further comprising methods for visualizing nucleic acids.

31. The method of claim 30, wherein the methods for visualizing nucleic acids comprise direct fluorescence hybridization.

32. The method of claim 26, wherein the oligonucleotide is single-stranded or double-stranded DNA, RNA, or a synthetic oligonucleotide.

33. The method of claim 32, wherein the synthetic oligonucleotide is a peptide nucleic acid.

34. The method of claim 26, wherein the target binding region is sequence specific.

35. The method of claim 26, further comprising measurement of target oligonucleotides in addition to protein, and wherein the target oligonucleotides comprise DNA, RNA, lincRNA, mRNA, viral RNAs, or a combination thereof.

36. The method of claim 26, wherein each protein binding molecule bound to an oligonucleotide is an oligonucleotide-tagged protein binding molecule that further comprises a poly-A sequence.

37. The method of claim 26, further comprising delivering one or more ligation dependent probes to the cells, wherein the one or more ligation dependent probe comprise i) sequences that bind in proximate locations on a target RNA, and ii) the first primer handle sequence, the second primer handle sequence, or both; linking the bound proximity probes; amplifying the oligonucleotide of the construct and the linked ligation dependent probes using barcoded PCR primers, wherein the barcode is incorporated into each resulting amplicon, and quantifying target protein abundance and/or determining target protein localization based at least in part on sequencing of amplicons.

38. The method of claim 37, wherein the one or more ligation dependent probes are linked by ligation, splinted ligation, hybridization, or proximity extension.

39. The method of claim 37, wherein the one or more ligation dependent probes are molecular inversion probes (MIPs), padlock probes, or split-ligation probes, each probe further comprising a unique molecular identifier (UMI).

40. The method of claim 26, further comprising admixing the population of cells with monomers of a polymerizable hydrogel and polymerizing the gel in an oil emulsion under conditions that allow covalent anchoring of nucleic acids and/or proteins to the hydrogel, wherein individual cells are encapsulated in the individual discrete volume;
breaking the emulsions to release the individual discrete volume;
adding oligonucleotide-tagged protein binding molecules, either before or after hydrogel polymerization;
performing PCR in the individual discrete volumes, wherein cell-barcoded amplicons are generated; and
sequencing the resulting amplicons.

41. The method of claim 26, wherein the cells are fixed before preparing the hydrogel droplets.

42. The method of claim 26, wherein the method allows for measuring of both intracellular and extracellular proteins.

43. A method for determining the quantity and location of proteins within single cells comprising
encapsulating cells or tissue in a hydrogel;
treating the cells or tissue with the construct of claim 1,
delivering one or more ligation dependent probes to the cells, wherein the ligation dependent probe comprises a sequence that is complementary to the first primer handle sequence and a sequence that is complementary to the second primer handle sequence;
amplifying the oligonucleotide of the construct using the ligation dependent probes, wherein the amplified oligonucleotide is incorporated into each resulting amplicon; and
quantifying target protein abundance and/or determining target protein localization based at least in part on sequencing of amplicons.

44. The method of claim 43, wherein the protein binding molecule is an antibody.

45. The method of claim 43 wherein the cells are fixed before delivering the ligation dependent probes.

46. The method of claim 43, wherein the amplification reagents are rolling circle amplification reagents.

47. The method of claim 43, wherein the ligation dependent probes are molecular inversion probes (MIPs), padlock probes, or split-ligation probes.

48. The method of claim 43, further comprising delivering one or more additional ligation dependent probes to the cells for measuring target mRNA.

49. The method of claim 43, wherein the individual discrete volumes are hydrogel droplets.

50. The method of claim 43, further comprising methods for visualizing proteins.

51. The method of claim 50, wherein the methods for visualizing proteins comprise in situ imaging.

52. The method of claim 43, further comprising a reporter sequence that enables cellular recording.

53. The method of claim 43, wherein amplicons are sequenced using a fluorescence in situ sequencing method.

54. A method for quantifying protein in individual molecule complexes comprising:
fixing a population of cells such that oligonucleotide-protein complexes are formed;
delivering the construct of claim 1 to the oligonucleotide-protein complexes;
encapsulating complexes in an individual discrete volume, wherein the individual discrete volume comprises PCR primers on a bead;
suspending the individual discrete volume in a reverse transcription mixture; and
detecting the nucleotide sequence of the origin specific barcode sequence, thereby assigning the target oligonucleotide and protein of interest to a specific individual discrete volume, while maintaining information about sample origin of the target oligonucleotide.

55. The method of claim 54, wherein the protein binding molecule is an antibody.

56. The method of claim 54, wherein detecting the nucleotide sequence of the origin specific barcode sequence comprises nucleic acid sequencing, amplification, hybridization, or any combination thereof.

57. The method of claim 54, wherein the individual discrete volume is a hydrogel droplet.

58. The method of claim 54, further comprising methods for visualizing nucleic acids.

59. The method of claim 58, wherein the methods for visualizing nucleic acids comprise direct fluorescence hybridization.

60. The method of claim 54, wherein the oligonucleotide is single-stranded or double-stranded DNA, RNA, or a synthetic oligonucleotide.

61. The method of claim 54, wherein the oligonucleotide comprises single-stranded RNA.

62. The method of claim 61, wherein the method comprises quantifying expression of single-stranded RNA, mRNA and genomic RNA simultaneously.

63. The method of claim 62, wherein the synthetic oligonucleotide is a peptide nucleic acid.

64. The method of claim 54, wherein the target binding region is sequence specific.

65. The method of claim 54, wherein the target oligonucleotide comprises DNA, RNA, lincRNA, mRNA, viral RNAs, or a combination thereof.

66. The method of claim 54, wherein each protein binding molecule bound to an oligonucleotide is an oligonucleotide-tagged protein binding molecule that further comprises a poly-A sequence.

67. The method of claim 54, further comprising admixing the oligonucleotide-protein complexes with monomers of a polymerizable hydrogel and polymerizing the gel in an oil emulsion under conditions that allow covalent anchoring of nucleic acids and/or proteins to the hydrogel, wherein individual complexes are encapsulated in the individual discrete volume;
breaking the emulsions to release the individual discrete volume;
adding oligonucleotide-tagged protein binding molecules, either before or after hydrogel polymerization;
performing PCR in the individual discrete volumes, wherein cell-barcoded amplicons are generated; and
sequencing the resulting amplicons.

68. The method of claim 54, wherein the complexes are fixed before preparing the hydrogel droplets.

69. The method of claim 54, wherein the method allows for measuring of both intracellular and extracellular proteins.

70. A method for quantifying protein in individual molecule complexes comprising:
fixing a population of cells, lysing the cells, and encapsulating the resulting individual molecule complexes with the construct of claim 1 in an individual discrete volume;
wherein the individual discrete volume comprises PCR primers on a bead;
amplifying the oligonucleotide of the construct using PCR; and
quantifying target protein abundance and/or determining target protein localization based at least in part on sequencing of amplicons.

71. The method of claim 70, wherein the protein binding molecule is an antibody.

72. The method of claim 70, wherein detecting the nucleotide sequence of the origin specific barcode sequence comprises nucleic acid sequencing, amplification, hybridization, or any combination thereof.

73. The method of claim 70, wherein the individual discrete volume is a hydrogel droplet.

74. The method of claim 70, further comprising methods for visualizing nucleic acids.

75. The method of claim 74, wherein the methods for visualizing nucleic acids comprise direct fluorescence hybridization.

76. The method of claim 70, wherein the oligonucleotide is single-stranded or double-stranded DNA, RNA, or a synthetic oligonucleotide.

77. The method of claim 76, wherein the synthetic oligonucleotide is a peptide nucleic acid.

78. The method of claim 70, wherein the target binding region is sequence specific.

79. The method of claim 70, further comprising measurement of target oligonucleotides in addition to protein, and wherein the target oligonucleotides comprise DNA, RNA, lincRNA, mRNA, viral RNAs, or a combination thereof.

80. The method of claim 70, wherein each protein binding molecule bound to an oligonucleotide is an oligonucleotide-tagged protein binding molecule that further comprises a poly-A sequence.

81. The method of claim 70, further comprising delivering one or more ligation dependent probes to the oligonucleotide-protein complexes, wherein the one or more ligation dependent probe comprises i) sequences that bind in proximate locations on a target RNA, and ii) the first primer handle sequence, the second primer handle sequence, or both, linking the bound proximity probes; amplifying the oligonucleotide of the construct and the linked ligation dependent probes using barcoded PCR primers, wherein the barcode is incorporated into each resulting amplicon, and quantifying target protein abundance and/or determining target protein localization based at least in part on sequencing of amplicons.

82. The method of claim 70, further comprising admixing the oligonucleotide-protein complexes with monomers of a polymerizable hydrogel and polymerizing the gel in an oil emulsion under conditions that allow covalent anchoring of nucleic acids and/or proteins to the hydrogel, wherein individual complexes are encapsulated in the individual discrete volume;

breaking the emulsions to release the individual discrete volume;

adding oligonucleotide-tagged protein binding molecules, either before or after hydrogel polymerization;

performing PCR in the individual discrete volumes, wherein cell-barcoded amplicons are generated; and sequencing the resulting amplicons.

83. The method of claim 70, wherein the cells are fixed before preparing the hydrogel droplets.

84. The method of claim 70, wherein the method allows for measuring of both intracellular and extracellular proteins.

85. A molecular assay system comprising
a) a plurality of constructs, wherein each construct of the plurality of constructs is according to claim 1;
b) amplification reagents; and
c) droplet forming reagents for formation of hydrogel-based droplets.

86. The system of claim 85, wherein the oligonucleotide-tagged protein binding molecules further comprise an adapter sequence.

87. The system of claim 85, wherein the oligonucleotide-tagged protein binding molecules further comprise a UMI.

88. The system of claim 85, wherein the protein binding molecules are antibodies, aptamers, peptides, avimers, small molecules, recombinant proteins, protein-binding derivatives, or nucleic acid molecules.

89. The system of claim 88, wherein the protein binding molecules are antibodies.

90. The system of claim 85, wherein the oligonucleotides comprise single-stranded RNA.

91. The system of claim 85, wherein the oligonucleotides comprise single-stranded or double-stranded DNA or synthetic oligonucleotides.

92. The system of claim 85, wherein the oligonucleotides further comprise a poly-A sequence.

93. The system of claim 85, wherein the first primer handle sequence comprises SEQ ID NO:1 and the second primer handle sequence comprises SEQ ID NO:2.

94. The system of claim 85, further comprising a set of ligation dependent probes.

95. The system of claim 85, wherein the amplification reagents are whole genome amplification reagents, PCR amplification reagent, reverse transcription reagents, rolling circle amplification reagents, or a combination thereof.

96. The system of claim 85, wherein the ligation dependent probes are molecular inversion probes (MIPs), padlock probes, or split-ligation probes.

97. A kit comprising
a) a panel of oligonucleotides, each oligonucleotide comprising an origin specific barcode sequence, a first primer handle sequence, a second primer handle sequence, and a target binding region, and wherein the first primer handle sequence, the second primer handle sequence or both are capable of binding a padlock probe;
b) a panel of protein binding molecules; and
c) optionally, reagents for coupling the protein binding molecules to the oligonucleotides.

98. A kit according to claim 97, wherein the oligonucleotides and the protein binding molecules are coupled together.

99. The kit of claim 97, wherein the protein binding molecules are antibodies, aptamers, peptides, avimers, small molecules, recombinant proteins, protein-binding derivatives, or nucleic acid molecules.

100. The kit of claim 97, wherein the protein binding molecules are antibodies.

101. The kit of claim 100, wherein the antibodies target receptors on immune cells.

102. The kit of claim 100, wherein the antibodies target specific markers in intracellular signaling pathways.

103. The kit of claim 100, wherein the antibodies target transcription factors.

\* \* \* \* \*

SEQUENCE LISTING

```
<160> NUMBER OF SEQ ID NOS: 4

<210> SEQ ID NO 1
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 1
cacccgagaa ttcca                                                    15

<210> SEQ ID NO 2
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 2
```

```
ctcgatagcc                                                              10

<210> SEQ ID NO 3
<211> LENGTH: 64
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (24)..(29)
<223> OTHER INFORMATION: N = any nucleotide

<400> SEQUENCE: 3
cacccgagaa ttccacctgg tagnnnnnnc tcgatagcca aaaaaaaaaa aaaaaaaaaa        60
aaaa                                                                    64

<210> SEQ ID NO 4
<211> LENGTH: 12
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(12)
<223> OTHER INFORMATION: N = any nucleotide

<400> SEQUENCE: 4
nnnnnnnnnn nn                                                           12
```